(12) United States Patent
Martin et al.

(10) Patent No.: US 6,696,608 B1
(45) Date of Patent: Feb. 24, 2004

(54) TRANSFER HYDROGENATION PROCESS

(75) Inventors: Juliette Martin, Huddersfield (GB); Lynne Alison Campbell, Grangemouth (GB)

(73) Assignee: Avecia Limited, Manchester (GB)

( * ) Notice: Subject to any disclaimer, the term of this patent is extended or adjusted under 35 U.S.C. 154(b) by 0 days.

(21) Appl. No.: 10/049,611

(22) PCT Filed: Jul. 25, 2000

(86) PCT No.: PCT/GB00/02867

§ 371 (c)(1),
(2), (4) Date: Feb. 14, 2002

(87) PCT Pub. No.: WO01/12574

PCT Pub. Date: Feb. 22, 2001

(30) Foreign Application Priority Data

Aug. 14, 1999 (GB) ................................. 9919118

(51) Int. Cl.$^7$ ..................... C07C 211/03; C07C 209/26
(52) U.S. Cl. ................... 564/336; 564/12; 564/397; 564/398; 564/428; 564/472
(58) Field of Search ................ 564/12, 336, 397, 564/398, 472, 428

(56) References Cited

FOREIGN PATENT DOCUMENTS

| EP | 0901996 A1 | 3/1999 |
|----|------------|--------|
| EP | 901996 | 3/1999 |
| WO | WO98/42643 | 10/1998 |
| WO | 98 42643 | 10/1998 |

OTHER PUBLICATIONS

Egushi, "Rational de novo design of NADH mimic for stereoselective reduction based on molecular orbital calculation", Tetrahedron, vol. 54, No. 5–6, pp. 705–714, 1998.
Uematsu, "Asmmetric Transfer Hydrogenation of Imines", J. Am. Chem. Soc, 1996, vol. 118, p. 4916–4917.
Kvintovics et al., "Amines as ligands in transfer hydrogenation catalysts", J. of Organometallic Chemistry, vol. 3761 (1989), pp. 117–122.
Eguchi et al., "Rational De Novo Design of NADH Mimic for Stereoselective Reduction Based on Molecular Orbital Calculation", Tetrahedron 54 (1998) pp. 705–714.
Uematsu et al., "Asymmetric Transfer Hydrogenation of Imines", J. Am. Chem. Soc. 118 (1996) pp. 4916–4917.

Primary Examiner—Shailendra Kumar
(74) Attorney, Agent, or Firm—Pillsbury Winthrop LLP

(57) ABSTRACT

A catalytic transfer hydrogenation process is provided. The process can be employed to transfer hydrogenate N-substituted imines and iminium salts, which are preferably prochiral. The catalyst employed in the process is preferably a metal complex with one hydrocarbyl or cyclopentadienyl ligand and which is also coordinated to defined bidentate ligands. Preferred metals include rhodium, ruthenium and iridium. Preferred bidentate ligands are diamines and aminoalcohols, particularly those comprising chiral centres. The hydrogen donor is advantageously a mixture of triethylamine and formic acid. A process for the production of primary and secondary amines using the catalytic transfer hydrogenation of the N-substituted imines and iminium salts is also provided.

20 Claims, No Drawings

TRANSFER HYDROGENATION PROCESS

CROSS REFERENCE TO RELATED APPLICATIONS

This application is a national phase application based on PCT/GB00/02867, filed Jul. 25, 2000, and which further claims priority from British Application No. 9919118.1, filed Aug. 14, 1999. These applications in their entirety are incorporated herein by reference.

This invention relates to catalytic transfer hydrogenation, particularly in the presence of a complexed transition metal, and to a process of making optically active compounds.

According to a first aspect of the present invention there is provided a process for the transfer hydrogenation of a substrate wherein the substrate is reacted with a hydrogen donor in the presence of a transfer hydrogenation catalyst, characterised in that the substrate has the general formula

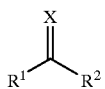

(1)

wherein:

X represents $NR^3$ or $(NR^4R^5)^+Q^-$;

$Q^-$ represents a monovalent anion;

$R^1$ and $R^2$ each independently represents a hydrogen atom, an optionally substituted hydrocarbyl, a perhalogenated hydrocarbyl, an optionally substituted heterocyclyl group, a substituted carbonyl functional group, a substituted thiocarbonyl functional group or substituted imino functional group, $R^1$ & $R^2$ optionally being linked in such a way as to form an optionally substituted ring;

$R^3$ and $R^4$ represents $-P(O)R^6R^7$, $-P(O)OR^8OR^9$, $-P(O)OR^8OH$, $-P(O)(OH)_2$, $-P(O)SR^{10}SR^{11}$, $-P(O)SR^{10}SH$, $-P(O)(SH)_2$, $-P(O)NR^{12}R^{13}NR^{14}R^{15}$, $-P(O)NR^{12}R^{13}NHR^{14}$, $-P(O)NHR^{12}NHR^{14}$, $-P(O)NR^{12}R^{13}NH_2$, $-P(O)NHR^{12}NH_2$, $-P(O)(NH_2)_2$, $-P(O)R^6OR^8$, $-P(O)R^6OH$, $-P(O)R^6SR^{10}$, $-P(O)R^6SH$, $-P(O)R^6NR^{12}R^{13}$, $-P(O)R^6NHR^{12}$, $-P(O)R^6NH_2$, $-P(O)OR^8SR^{10}$, $-P(O)OR^8SH$, $-P(O)OHSR^{10}$, $-P(O)OHSH$, $-P(O)OR^8NR^{12}R^{13}$, $-P(O)OR^8NHR^{12}$, $-P(O)OR^8NH_2$, $-P(O)OHNR^{12}R^{13}$, $-P(O)OHNHR^{12}$, $-P(O)OHNH_2$, $-P(O)SR^{10}NR^{12}R^{13}$, $-P(O)SR^{10}NHR^{12}$, $-P(O)SR^{10}NH_2$, $-P(O)SHNR^{12}R^{13}$, $-P(O)SHNHR^{12}$, $-P(O)SHNH_2$, $-P(S)R^6R^7$, $-P(S)OR^8OR^9$, $-P(S)OR^8OH$, $-P(S)(OH)_2$, $-P(S)SR^{10}SR^{11}$, $-P(S)SR^{10}SH$, $-P(S)(SH)_2$, $-P(S)NR^{12}R^{13}NR^{14}R^{15}$, $-P(S)NR^{12}R^{13}NHR^{14}$, $-P(S)NHR^{12}NHR^{14}$, $-P(S)NR^{12}R^{13}NH_2$, $-P(S)NHR^{12}NH_2$, $-P(S)(NH_2)_2$, $-P(S)R^6OR^8$, $-P(S)R^6OH$, $-P(S)R^6SR^{10}$, $-P(S)R^6SH$, $-P(S)R^6NR^{12}R^{13}$, $-P(S)R^6NHR^{12}$, $-P(S)R^6NH_2$, $-P(S)OR^8SR^{10}$, $-P(S)OHSR^{10}$, $-P(S)OR^8SH$, $-P(S)OHSH$, $-P(S)OR^8NR^{12}R^{13}$, $-P(S)OR^8NHR^{12}$, $-P(S)OR^8NH_2$, $-P(S)OHNR^{12}R^{13}$, $-P(S)OHNHR^{12}$, $-P(S)OHNH_2$, $-P(S)SR^{10}NR^{12}R^{13}$, $-P(S)SR^{10}NHR^{12}$, $-P(S)SR^{10}NH_2$, $-P(S)SHNR^{12}R^{13}$, $-P(S)SHNHR^{12}$, $-P(S)SHNH_2$, $-PR^6R^7$, $-POR^8OR^9$, $-PSR^{10}SR^{11}$, $-PNR^{12}R^{13}NR^{14}R^{15}$, $-PR^6OR^8$, $-PR^6SR^{10}$, $-PR^6NR^{12}R^{13}$, $-POR^8SR^{10}$, $-POR^8NR^{12}R^{13}$, $-PSR^{10}NR^{12}R^{13}$, $-S(O)R^{16}$, $-S(O)_2R^{17}$, $-COR^{18}$, $-CO_2R^{19}$, or $SiR^{20}R^{21}R^{22}$;

$R^5$ represents a hydrogen atom, an optionally substituted hydrocarbyl, a perhalogenated hydrocarbyl, or an optionally substituted heterocyclyl group;

$R^6$ and $R^7$ independently represent an optionally substituted hydrocarbyl, a perhalogenated hydrocarbyl, an optionally substituted heterocyclyl group or $-N=CR^{23}R^{24}$ where $R^{23}$ and $R^{24}$ are as defined for $R^1$; and $R^8$ to $R^{22}$ each independently represents an optionally substituted hydrocarbyl, a perhalogenated hydrocarbyl or an optionally substituted heterocyclyl group, one or more of $R^1$ & $R^6$, $R^2$ & $R^7$, $R^6$ & $R^7$, $R^6$ & $R^8$, $R^6$ & $R^{10}$, $R^6$ & $R^{12}$, $R^1$ & $R^8$, $R^2$ & $R^9$, $R^8$ & $R^9$, $R^8$ & $R^{10}$, $R^8$ & $R^{12}$, $R^1$ & $R^{10}$, $R^2$ & $R^{11}$, $R^{10}$ & $R^{11}$, $R^{10}$ & $R^{12}$, $R^1$ & $R^{12}$, $R^2$ & $R^{13}$, $R^{12}$ & $R^{13}$, $R^1$ & $R^{14}$, $R^2$ & $R^{15}$, $R^{14}$ & $R^{15}$, $R^{12}$ & $R^{14}$, $R^1$ & $R^{16}$, $R^1$ & $R^{18}$, $R^1$ & $R^{19}$, $R^1$ & $R^{20}$, $R^2$ & $R^{21}$, $R^{20}$ & $R^{21}$ and $R^{21}$ & $R^{22}$ optionally being linked in such a way as to form an optionally substituted ring(s).

When X represents $(NR^4R^5)^+Q^-$, compounds of formula (1) are iminium salts. Iminium salts include protonated iminium salts and quaternary iminium salts. Quaternary iminium salts are represented by compounds of formula (I) in which $R^5$ is not hydrogen.

Anions which may be represented by $Q^-$ include halides, optionally substituted arylsulphonates, such as optionally substituted phenyl and naphthyl sulphonates, optionally substituted alkylsulphonates including halogenated alkylsulphonates, such as $C_{1-20}$alkylsulphonates, optionally substituted carboxylates, such as $C_{1-10}$ alkyl and aryl carboxylates, ions derived from the polyhalogenation of boron, phosphorous or antimony, and other common inorganic ions for example perchlorate. Particular examples of anions are bromide, chloride, iodide, hydrogen sulphate, tosylate, formate, acetate, tetrafluoroborate, hexafluorophosphate, hexafluoroantimonate, perchlorate, trifluoromethanesulphonate and trifluoroacetate. Preferred anions include bromide, chloride, iodide, formate and trifluoroacetate, and particularly preferred anions include iodide, formate and trifluoroacetate.

Hydrocarbyl groups which may be represented by one or more of $R^1$, $R^2$, and $R^5$ to $R^{24}$, include alkyl, alkenyl, alkynyl and aryl groups, and any combination thereof, such as aralkyl and alkaryl, for example benzyl groups.

Alkyl groups which may be represented by one or more of $R^1$, $R^2$, and $R^5$ to $R^{24}$ include linear and branched alkyl groups comprising up to 20 carbon atoms, particularly from 1 to 7 carbon atoms and preferably from 1 to 5 carbon atoms. When the alkyl groups are branched, the groups often comprise up to 10 branched chain carbon atoms, preferably up to 4 branched chain atoms. In certain embodiments, the alkyl group may be cyclic, commonly comprising from 3 to 10 carbon atoms in the largest ring and optionally featuring one or more bridging rings. Examples of alkyl groups which may be represented by $R^1$, $R^2$, and $R^5$ to $R^{24}$ include methyl, ethyl, propyl, 2-propyl, butyl, 2-butyl, t-butyl and cyclohexyl groups.

Alkenyl groups which may be represented by one or more of $R^1$, $R^2$, and $R^5$ to $R^{24}$ include $C_{2-20}$, and preferably $C_{2-6}$ alkenyl groups. One or more carbon-carbon double bonds may be present. The alkenyl group may carry one or more substituents, particularly phenyl substituents. Examples of alkenyl groups include vinyl, styryl and indenyl groups. When either of $R^1$ or $R^2$ represents an alkenyl group, a carbon-carbon double bond is preferably located at the position β to the C=X moiety. When either of $R^1$ or $R^2$ represents an alkenyl group, the compound of formula (1) is preferably an α,β-unsaturated iminium compound.

Alkynyl groups which may be represented by one or more of $R^1$, $R^2$, and $R^5$ to $R^{24}$ include $C_{2-20}$, and preferably $C_{2-10}$ alkynyl groups. One or more carbon-carbon triple bonds may be present. The alkynyl group may carry one or more substituents, particularly phenyl substituents. Examples of alkynyl groups include ethynyl, propyl and phenylethynyl groups. When either of $R^1$ or $R^2$ represents an alkynyl group, a carbon-carbon triple bond is preferably located at the position β to the C=X moiety. When either of $R^1$ or $R^2$ represents an alkynyl group, the compound of formula (1) preferably has the triple bond in conjugation with the iminium group.

Aryl groups which may be represented by one or more of $R^1$, $R^2$, and $R^5$ to $R^{24}$ may contain 1 ring or 2 or more fused rings which may include cycloalkyl, aryl or heterocyclic rings. Examples of aryl groups which may be represented by $R^1$, $R^2$, and $R^5$ to $R^{24}$ include phenyl, tolyl, fluorophenyl, chlorophenyl, bromophenyl, trifluoromethylphenyl, anisyl, naphthyl and ferrocenyl groups.

Perhalogenated hydrocarbyl groups which may be represented by one or more of $R^1$, $R^2$, and $R^5$ to $R^{24}$ independently include perhalogenated alkyl and aryl groups, and any combination thereof, such as aralkyl and alkaryl groups. Examples of perhalogenated alkyl groups which may be represented by $R^1$, $R^2$, and $R^5$ to $R^{24}$ include $-CF_3$ and $-C_2F_5$.

Heterocyclic groups which may be represented by one or more of $R^1$, $R^2$, and $R^5$ to $R^{24}$ independently include aromatic, saturated and partially unsaturated ring systems and may comprise 1 ring or 2 or more fused rings which may include cycloalkyl, aryl or heterocyclic rings. The heterocyclic group will contain at least one heterocyclic ring, the largest of which will commonly comprise from 3 to 7 ring atoms in which at least one atom is carbon and at least one atom is any of N, O, S or P. When either of $R^1$ or $R^2$ represents or comprises a heterocyclic group, the atom in $R^1$ or $R^2$ bonded to the C=X group is preferably a carbon atom. Examples of heterocyclic groups which may be represented by $R^1$, $R^2$, and $R^5$ to $R^{24}$ include pyridyl, pyrimidyl, pyrrolyl, thiophenyl, furanyl, indolyl, quinolyl, isoquinolyl, imidazoyl and triazoyl groups.

When any of $R^1$, $R^2$, and $R^5$ to $R^{24}$ is a substituted hydrocarbyl or heterocyclic group, the substituent(s) should be such so as not to adversely affect the rate or stereoselectivity of the reaction. Optional substituents include halogen, cyano, nitro, hydroxy, amino, imino, thiol, acyl, hydrocarbyl, perhalogenated hydrocarbyl, heterocyclyl, hydrocarbyloxy, mono or di-hydrocarbylamino, hydrocarbylthio, esters, carboxy, carbonates, amides, sulphonyl and sulphonamido groups wherein the hydrocarbyl groups are as defined for $R^1$ above. One or more substituents may be present. $R^1$, $R^2$, and $R^5$ to $R^{24}$ may each contain one or more chiral centres.

When any of $R^1$ & $R^2$, $R^1$ & $R^6$, $R^2$ & $R^7$, $R^1$ & $R^7$, $R^6$ & $R^8$, $R^6$ & $R^{10}$, $R^6$ & $R^{12}$, $R^1$ & $R^8$, $R^2$ & $R^9$, $R^8$ & $R^9$, $R^8$ & $R^{10}$, $R^8$ & $R^{12}$, $R^1$ & $R^{10}$, $R^2$ & $R^{11}$, $R_{10}$ & $R_{11}$, $R^{10}$ & $R^{12}$, $R^1$ & $R^{12}$, $R^2$ & $R^{13}$, $R^{12}$ & $R^{13}$, $R^1$ & $R^{14}$, $R^2$ & $R^{15}$, $R^{14}$ & $R^{15}$, $R^{12}$ & $R^{14}$, $R^1$ & $R^{16}$, $R_1$ & $R^{18}$, $R^1$ & $R^{19}$, $R^1$ & $R^{20}$, $R^2$ & $R^{21}$, $R^{20}$ & $R^{21}$ and $R^{21}$ & $R^{22}$ are linked in such a way that when taken together with the atoms to which they are attached that a ring is formed, it is preferred that these be 5, 6 or 7 membered rings. The rings formed in this way may additionally be fused to each other or to other ring systems. Examples of rings which may be so formed include oxazaphospholidenes, dioxaphospholans, phospholans, phosphorinans, dioxaphosphorinans and benzodioxaphospholans. The rings may be optionally substituted or may be fused to other rings.

Substituted carbonyl functional groups which may be represented by one or more of $R^1$, $R^2$, $R^{23}$ and $R^{24}$ include aldehyde, ketone, acid and ester groups, for example $-COR^{25}$, $-CO_2R^{25}$, and $-CONR^{25}R^{26}$ wherein $R^{25}$ and $R^{26}$ independently represent hydrogen, an optionally substituted hydrocarbyl, a perhalogenated hydrocarbyl or an optionally substituted heterocyclyl group as defined hereinbefore for $R^5$.

Substituted thiocarbonyl functional groups which may be represented by one or more of $R^1$, $R^2$, $R^{23}$ and $R^{24}$ include thioaldehyde, thioketone, thioacid and thioester groups, for example $-CSR^{25}$, $-CSOR^{25}$ and $-CSNR^{25}R^{26}$ wherein $R^{25}$ and $R^{26}$ independently represent hydrogen; an optionally substituted hydrocarbyl, a perhalogenated hydrocarbyl or an optionally substituted heterocyclyl group as defined hereinbefore for $R^5$.

Substituted imino functional groups which may be represented by one or more of $R^1$, $R^2$, $R^{23}$ and $R^{24}$ include unsubstituted imines and substituted imine and iminium groups, for example $-C(=NR^{25})R^{26}$ and $-C(=X)R^{26}$ wherein X is as hereinbefore defined and $R^{25}$ and $R^{26}$ independently represent hydrogen, an optionally substituted hydrocarbyl, a perhalogenated hydrocarbyl or an optionally substituted heterocyclyl group as defined hereinbefore for $R^5$.

When one of $R^1$ or $R^2$ is represented by a group selected from a carbonyl functional group, a thiocarbonyl functional group and an imino functional group, it is preferred that the other of $R^1$ or $R^2$ is represented by a hydrogen atom, an optionally substituted hydrocarbyl group, a perhalogenated hydrocarbyl group or an optionally substituted heterocyclyl group.

When one of $R^{23}$ or $R^{24}$ is represented by a group selected from a carbonyl functional group, a thiocarbonyl functional group and an imino functional group, it is preferred that the other of $R^{23}$ or $R^{24}$ being represented by a hydrogen atom, an optionally substituted hydrocarbyl group, a perhalogenated hydrocarbyl group or an optionally substituted heterocyclyl group.

When one of $R^1$ & $R^6$ or $R^2$ & $R^7$ is linked in such a way as to form an optionally substituted ring and the ring so formed contains more than one carbon nitrogen double bond (imino group), it is preferred that nitrogen-phosphorous heterocycle so formed has both nitrogens are attached to a common phosphorous atom. Examples of such nitrogen-phosphorous heterocycles include

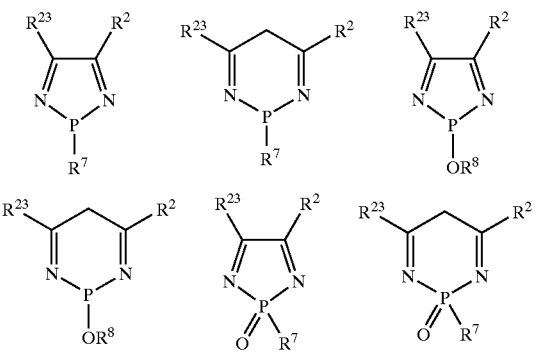

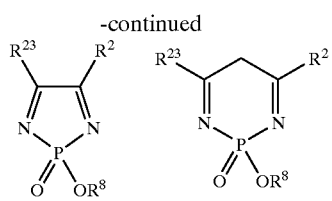

In certain preferred embodiments, $R^1$, $R^2$, and $R^5$ to $R^{24}$ are all independently $C_{1-6}$alkyl or are a combination of aryl, particularly phenyl, $C_{1-6}$alkyl and $C_{6-10}$aralkyl. Substituents may be present, particularly substituents para to the C=X group when one or more of $R^1$, $R^2$, and $R^5$ to $R^{24}$ is a phenyl group.

In many preferred embodiments, when $R^3$ or $R^4$ is a group selected from —P(O)$R^6R^7$, —P(O)O$R^8$O$R^9$, —P(O)O$R^8$OH, —P(O)S$R^{10}$S$R^{11}$, —P(O)S$R^{10}$SH, —P(O)N$R^{12}R^{13}$N$R^{14}R^{15}$, —P(O)N$R^{12}R^{13}$NH$R^{14}$, —P(O)NH$R^{12}$NH$R^{14}$, —P(O)N$R^{12}R^{13}$NH$_2$, —P(O)NH$R^{12}$NH$_2$, —P(O)$R^6$O$R^8$, —P(O)$R^6$OH, —P(O)$R^6$S$R^{10}$, —P(O)$R^6$SH, —P(O)$R^6$N$R^{12}R^{13}$, —P(O)$R^6$NH$R^{12}$, —P(O)$R^6$NH$_2$, —P(O)O$R^8$S$R^{10}$, —P(O)O$R^8$SH, —P(O)OHS$R^{10}$, —P(O)O$R^8$N$R^{12}R^{13}$, —P(O)O$R^8$NH$R^{12}$, —P(O)O$R^8$NH$_2$, —P(O)OHN$R^{12}R^{13}$, —P(O)OHNH$R^{12}$, —P(O)S$R^{10}$N$R^{12}R^{13}$, —P(O)S$R^{10}$NH$R^{12}$, —P(O)S$R^{10}$NH$_2$, —P(O)SHN$R^{12}R^{13}$, —P(O)SHNH$R^{12}$, —P(S)$R^6R^7$, —P(S)O$R^8$O$R^9$, —P(S)O$R^8$OH, —P(S)S$R^{10}$S$R^{11}$, —P(S)S$R^{10}$SH, —P(S)(SH)$_2$, —P(S)N$R^{12}R^{13}$N$R^{14}R^{15}$, —P(S)N$R^{12}R^{13}$NH$R^{14}$, —P(S)NH$R^{12}$NH$R^{14}$, —P(S)N$R^{12}R^{13}$NH$_2$, —P(S)NH$R^{12}$NH$_2$, —P(S)$R^6$O$R^8$, —P(S)$R^6$OH, —P(S)$R^6$S$R^{10}$, —P(S)$R^6$SH, —P(S)$R^6$N$^{12}R^{13}$, —P(S)$R^6$NH$R^{12}$, —P(S)$R^6$NH$_2$, —P(S)O$R^8$S$R^{10}$, —P(S)OHS$R^{10}$, —P(S)O$R^8$SH, —P(S)O$R^8$N$R^{12}R^{13}$, —P(S)O$R^8$NH$R^{12}$, —P(S)O$R^8$NH$_2$, —P(S)OHN$R^{12}R^{13}$, —P(S)OHNH$R^{12}$, —P(S)S$R^{10}$N$R^{12}R^{13}$, —P(S)S$R^{10}$NH$R^{12}$, —P(S)S$R^{10}$NH$_2$, —P(S)SHN$R^{12}R^{13}$, —P(S)SHNH$R^{12}$, —P$R^6R^7$, —PO$R^8$O$R^9$, —PS$R^{10}$S$R^{11}$, —PN$R^{12}R^{13}$N$R^{14}R^{15}$, —P$R^6$O$R^8$, —P$R^6$S$R^{10}$, —P$R^6$N$R^{12}R^{13}$, —PO$R^8$S$R^{10}$, —PO$R^8$N$R^{12}R^{13}$, —PS$R^{10}$N$R^{12}R^{13}$, or Si$R^{20}R^{21}R^{22}$, the groups $R^6$ to $R^{15}$ and $R^{20}$ to $R^{22}$ are selected to be the same and more preferably they are selected to all be phenyl or ethyl groups. This may have the advantage that synthesis of intermediates is simplified. However, in certain embodiments it may be preferable for more than one of the groups $R^6$ to $R^{15}$ or $R^{20}$ to $R^{22}$ present to be different, in which case it is most preferable that each $R^6$ to $R^{15}$ or $R^{20}$ to $R^{22}$ group present is selected to be one of methyl, ethyl, propyl, i-propyl, butyl, sec-butyl, t-butyl or phenyl.

Preferably, $R^3$ and $R^4$ are electron withdrawing groups, such as —P(O)$R^6R^7$, —P(O)O$R^8$O$R^9$, —P(O)O$R^8$OH, —P(O)(OH)$_2$, —P(O)S$R^{10}$S$R^{11}$, —P(O)S$R^{10}$SH, —P(O)(SH)$_2$, —P(O)N$R^{12}R^{13}$N$R^{14}R^{15}$, —P(O)N$R^{12}R^{13}$NH$R^{14}$, —P(O)NH$R^{12}$NH$R^{14}$, —P(O)N$R^{12}R^{13}$NH$_2$, —P(O)NH$R^{12}$NH$_2$, —P(O)(NH$_2$)$_2$, —P(O)$R^6$O$R^8$, —P(O)$R^6$OH, —P(O)$R^6$S$R^{10}$, —P(O)$R^6$SH, —P(O)$R^6$N$R^{12}R^{13}$, —P(O)$R^6$NH$R^{12}$, —P(O)$R^6$NH$_2$, —P(O)O$R^8$S$R^{10}$, —P(O)O$R^8$SH, —P(O)OHS$R^{10}$, —P(O)OHSH, —P(O)O$R^8$N$R^{12}R^{13}$, —P(O)O$R^8$NH$R^{12}$, —P(O)O$R^8$NH$_2$, —P(O)OHN$R^{12}R^{13}$, —P(O)OHNH$R^{12}$, —P(O)OHNH$_2$, —P(O)S$R^{10}$N$R^{12}R^{13}$, —P(O)S$R^{10}$NH$R^{12}$, —P(O)S$R^{10}$NH$_2$, —P(O)SHN$R^{12}R^{13}$, —P(O)SHNH$R^{12}$, —P(O)SHNH$_2$, —P(S)$R^6R^7$, —P(S)O$R^8$O$R^9$, —P(S)O$R^8$OH, —P(S)(OH)$_2$, —P(S)S$R^{10}$S$R^{11}$, —P(S)S$R^{10}$SH, —P(S)(SH)$_2$, —P(S)N$R^{12}R^{13}$N$R^{14}R^{15}$, —P(S)N$R^{12}R^{13}$NH$R^{14}$, —P(S)NH$R^{12}$NH$R^{14}$, —P(S)N$R^{12}R^{13}$NH$_2$, —P(S)NH$R^{12}$NH$_2$, —P(S)(NH$_2$)$_2$, —P(S)$R^6$O$R^8$, —P(S)$R^6$OH, —P(S)$R^6$S$R^{10}$, —P(S)$R^6$SH, —P(S)$R^6$N$R^{12}R^{13}$, —P(S)$R^6$NH$R^{12}$, —P(S)$R^6$NH$_2$, —P(S)O$R^8$S$R^{10}$, —P(S)OHS$R^{10}$, —P(S)O$R^8$SH, —P(S)OHSH, —P(S)O$R^8$N$R^{12}R^{13}$, —P(S)O$R^8$NH$R^{12}$, —P(S)O$R^8$NH$_2$, —P(S)OHN$R^{12}R^{13}$, —P(S)OHNH$R^{12}$, —P(S)OHNH$_2$, —P(S)S$R^{10}$N$R^{12}R^{13}$, —P(S)S$R^{10}$NH$R^{12}$, —P(S)S$R^{10}$NH$_2$, —P(S)SHN$R^{12}R^{13}$, —P(S)SHNH$R^{12}$, —P(S)SHNH$_2$, —S(O)$R^{16}$, —S(O)$_2R^{17}$ —CO$R^{18}$, and —CO$_2R^{19}$. It is especially preferred that $R^3$ and $R^4$ are groups selected from —P(O)$R^6R^7$, —P(O)O$R^8$O$R^9$, —P(O)$R^6$O$R^8$, —P(S)$R^6R^7$, —P(S)O$R^8$O$R^9$, —P(S)$R^6$O$R^8$, —S(O)$R^{16}$, —CO$R^{18}$, and —CO$_2R^{19}$. It is most preferred that $R^3$ and $R^4$ are groups selected from —P(O)$R^6R^7$, —P(O)O$R^8$O$R^9$.

When either $R^3$ or $R^4$ is a group selected from —P(O)$R^6R^7$, —P(O)O$R^8$O$R^9$, —P(O)O$R^8$OH, —P(O)S$R^{10}$S$R^{11}$, —P(O)S$R^{10}$SH, —P(O)N$R^{12}R^{13}$N$R^{14}R^{15}$, —P(O)N$R^{12}R^{13}$NH$R^{14}$, —P(O)NH$R^{12}$NH$R^{14}$, —P(O)N$R^{12}R^{13}$NH$_2$, —P(O)NH$R^{12}$NH$_2$, —P(O)$R^6$O$R^8$, —P(O)$R^6$OH, —P(O)$R^6$S$R^{10}$, —P(O)$R^6$SH, —P(O)$R^6$N$R^{12}R^{13}$, —P(O)$R^6$NH$R^{12}$, —P(O)$R^6$NH$_2$, —P(O)O$R^8$S$R^{10}$, —P(O)O$R^8$SH, —P(O)OHS$R^{10}$, —P(O)O$R^8$N$R^{12}R^{13}$, —P(O)O$R^8$NH$R^{12}$, —P(O)O$R^{10}$NH$_2$, —P(O)OHN$R^{12}R^{13}$, —P(O)OHNH$R^{12}$, —P(O)S$R^{10}$N$R^{12}R^{13}$, —P(O)S$R^{10}$NH$R^{12}$, —P(O)S$R^{10}$NH$_2$, —P(O)SHN$R^{12}R^{13}$, —P(O)SHNH$R^{12}$, —P(S)$R^6R^7$, —P(S)O$R^8$O$R^9$, —P(S)O$R^8$OH, —P(S)S$R^{10}$S$R^{11}$, —P(S)S$R^{10}$SH, —P(S)(SH)$_2$, —P(S)N$R^{12}R^{13}$N$R^{14}R^{15}$, —P(S)N$R^{12}R^{13}$NH$R^{14}$, —P(S)NH$R^{12}$NH$R^{14}$, —P(S)N$R^{12}R^{13}$NH$_2$, —P(S)NH$R^{12}$NH$_2$, —P(S)$R^6$O$R^8$, —P(S)$R^6$OH, —P(S)$R^6$S$R^{10}$, —P$^6$SH, —P(S)$R^6$N$R^{12}R^{13}$, —P(S)$R^6$NH$R^{12}$, —P(S)$R^6$NH$_2$, —P(S)O$R^8$S$R^{10}$, —P(S)OHS$R^{10}$, —P(S)O$R^8$SH, —P(S)O$R^8$N$R^{12}R^{13}$, —P(S)O$R^8$NH$R^{12}$, —P(S)O$R^8$NH$_2$, —P(S)OHN$R^{12}R^{13}$, —P(S)OHNH$R^{12}$, —P(S)S$R^{10}$N$R^{12}R^{13}$, —P(S)S$R^{10}$NH$R^{12}$, —P(S)S$R^{10}$NH$_2$, —P(S)SHN$R^{12}R^{13}$, —P(S)SHNH$R^{12}$, —P$R^6R^7$, —PO$R^8$O$R^9$, —PS$R^{10}$S$R^{11}$, —PN$R^{12}R^{13}$N$R^{14}R^{15}$, —P$R^6$O$R^8$, —P$R^6$S$R^{10}$, —P$R^6$N$R^{12}R^{13}$, —PO$R^8$S$R^{10}$, —PO$R^8$N$R^{12}R^{13}$, —PS$R^{10}$N$R^{12}R^{13}$, —S(O)$R^{16}$, —S(O)$_2R^{17}$, —CO$R^{18}$, —CO$_2R^{19}$, it is preferred that the groups represented by $R^6$ to $R^{19}$ are independently selected from alkyl or aryl groups, for example methyl, ethyl, propyl, i-propyl, butyl, sec-butyl, t-butyl and phenyl groups, and preferably $C_{1-6}$alkyl or $C_{6-12}$aryl groups.

The groups $R^6$ to $R^{22}$ may contain chiral centres, or may be selected such that the atom to which they are bonded is a chiral centre.

In certain preferred embodiments, one of $R^1$ and $R^2$ is an alkyl group and the other is aryl or heterocyclyl, X is N$R^3$ where $R^3$ is either —P(O)$R^6R^7$ or —P(O)O$R^8$O$R^9$ wherein $R^6$ to $R^9$ is an alkyl or aryl group, more preferably a $C_{1-4}$alkyl group, a phenyl group or a phenyl group substituted with one or more $C_{1-4}$alkyl groups.

Most advantageously, the compound of formula (1) is prochiral, such that the hydrogenated product comprises a chiral atom to which $R^1$, $R^2$ and X are each bonded. Such an asymmetric transfer hydrogenation process forms an especially preferred aspect of the present invention. Most commonly, when the compound of formula (1) is prochiral, $R^1$ and $R^2$ are different, and neither is hydrogen. Preferably, one of $R^1$ and $R^2$ is aliphatic and the other is aryl or heterocyclyl.

Examples of compounds of formula (1) include

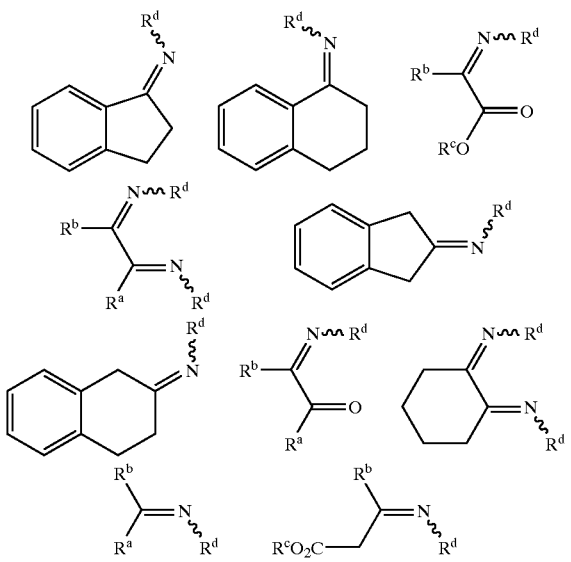

wherein:

$R^a$=Ph, Naphthyl, $CH_2Ph$, hexyl, iPr, tBu, Et, or Me $R^b$=Ph, Naphthyl, $CH_2Ph$, hexyl, iPr, tBu, Et, or Me $R^c$=Ph, Naphthyl, $CH_2Ph$, hexyl, iPr, tBu, Et, or Me; and $R^d$=$PO(Ph)_2$, or $PO(Et)_2$.

Hydrogen donors include hydrbgen, primary and secondary alcohols, primary and secondary amines, carboxylic acids and their esters and amine salts, readily dehydrogenatable hydrocarbons, clean reducing agents, and any combination thereof.

Primary and secondary alcohols which may be employed as hydrogen donors comprise commonly from 1 to 10 carbon atoms, preferably from 2 to 7 carbon atoms, and more preferably 3 or 4 carbon atoms. Examples of primary and secondary alcohols which may be represented as hydrogen donors include methanol, ethanol, propan-1-ol, propan-2-ol, butan-1-ol, butan-2-ol, cyclopentanol, cyclohexanol, benzylalcohol, and menthol. When the hydrogen donor is an alcohol, secondary alcohols are preferred, especially propan-2-ol and butan-2-ol.

Primary and secondary amines which may be employed as hydrogen donors comprise commonly from 1 to 20 carbon atoms, preferably from 2 to 14 carbon atoms, and more preferably 3 or 8 carbon atoms. Examples of primary and secondary amines which may be represented as hydrogen donors include ethylamine, propylamine, isopropylamine, butylamine, isobutylamine, dihexylamine, diethylamine, dipropylamine, di-isopropylamine, dibutylamine, di-isobutylamine, dihexylamine, benzylamine, dibenzylamine and piperidine. When the hydrogen donor is an amine, primary amines are preferred, especially primary amines comprising a secondary alkyl group, particularly isopropylamine and isobutylamine.

Carboxylic acids or their esters which may be employed as hydrogen donors comprise commonly from 1 to 10 carbon atoms, preferably from 1 to 3 carbon atoms. In certain embodiments, the carboxylic acid is advantageously a beta-hydroxy-carboxylic acid. Esters may be derived from the carboxylic acid and a $C_{1-10}$ alcohol. Examples of carboxylic acids which may be employed as hydrogen donors include formic acid, lactic acid, ascorbic acid and mandelic acid. The most preferred carboxylic acid is formic acid. In certain preferred embodiments, when a carboxylic acid is employed as hydrogen donor, at least some of the carboxylic acid is preferably present as salt, preferably an amine, ammonium or metal salt. Preferably, when a metal salt is present the metal is selected form the alkali or alkaline earth metals of the periodic table, and more preferably is selected from the group I elements, such as lithium, sodium or potassium. Amines which may be used to form such salts include both aromatic and non-aromatic amines, also primary, secondary and tertiary amines and comprise typically from 1 to 20 carbon atoms. Tertiary amines, especially trialkylamines, are preferred. Examples of amines which may be used to form salts include trimethylamine, triethylamine, di-isopropylethylamine and pyridine. The most preferred amine is triethylamine. When at least some of the carboxylic acid is present as an amine salt, particularly when a mixture of formic acid and triethylamine is employed, the mole ratio of acid to amine is between 1:1 and 50:1 and preferably between 1:1 and 10:1, and most preferably about 5:2. When at least some of the carboxylic acid is present as a metal salt, particularly when a mixture of formic acid and a group I metal salt is employed, the mole ratio of acid to metal ions present is between 1:1 and 50:1 and preferably between 1:1 and 10:1, and most preferably about 2:1. The ratios of acid to salts may be maintained during the course of the reaction by the addition of either component, but usually by the addition of the carboxylic acid.

Readily dehydrogenatable hydrocarbons which may be employed as hydrogen donors comprise hydrocarbons which have a propensity to aromatise or hydrocarbons which have a propensity to form highly conjugated systems. Examples of readily dehydrogenatable hydrocarbons which may be employed by as hydrogen donors include cyclohexadiene, cyclohexene, tetralin, dihydrofuran and terpenes.

Clean reducing agents which may be represented as hydrogen donors comprise reducing agents with a high reduction potential, particularly those having a reduction potential relative to the standard hydrogen electrode of greater than about $-0.1$ eV, often greater than about $-0.5$ eV, and preferably greater than about $-1$ eV. Examples of clean reducing agents which may be represented as hydrogen donors include hydrazine and hydroxylamine.

The most preferred hydrogen donors are propan-2-ol, butan-2-ol, triethylammonium formate and a mixture of triethylammonium formate and formic acid.

Transfer hydrogenation catalysts may include such catalysts such as a) the chiral Ruthenium (II) catalysts developed for ketone reduction which are disclosed in Chem. Rev., 1998, 98, 2607 see Table 2; b) the Zhang tridentate bis (oxazolinylmethyl)amine catalysts and related catalysts as disclosed in J. Am. Chem. Soc., 1998, 120, 3817, Tet. Let., 1997, 38(37), 6565 and in WO99/24410 (particularly the bis(phenyloxazolin-2-yl)amine and related catalysts discussed therein); and c) the transition metal, particularly group VIII metal, complexes with chiral ligands of formula

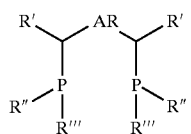

wherein AR is any aromatic or ring structure and R', R" and R'" are each independently selected from aryl, alkyl, aralkyl, ring-substituted aralkyl, substituted aryl and combinations thereof as disclosed in U.S. Pat. No. 5,767,276, the catalysts of a), b) and c) being incorporated herein by reference.

Preferred transfer hydrogenation catalysts for use in the process of the present invention have the general formula:

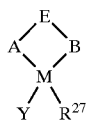

wherein:

$R^{27}$ represents a neutral optionally substituted hydrocarbyl, a neutral optionally substituted perhalogenated hydrocarbyl, or an optionally substituted cyclopentadienyl ligand;

A represents $-NR^{28}-$, $-NR^{29}-$, $-NHR^{28}$, $-NR^{28}R^{29}$ or $-NR^{29}R^{30}$ where $R^{28}$ is H, $C(O)R^{30}$, $SO_2R^{30}$, $C(O)NR^{30}R^{34}$, $C(S)NR^{30}R^{34}$, $C(=NR^{34})SR^{35}$ or $C(=NR^{34})OR^{35}$, $R^{29}$ and $R^{30}$, each independently represents an optionally substituted hydrocarbyl, perhalogenated hydrocarbyl or an optionally substituted heterocyclyl group, and $R^{34}$ and $R^{35}$ are each independently hydrogen or a group as defined for $R^{30}$;

B represents $-O-$, $-OH$, $OR^{31}$, $-S-$, $-SH$, $SR^{31}$, $-NR^{31}-$, $-NR^{32}-$, $-NHR^{32}$, $-NR^{31}R^{32}$, $-NR^{31}R^{33}$, $-PR^{31}-$ or $-PR^{31}R^{33}$ where $R^{32}$ is H, $C(O)R^{33}$, $SO_2R^{33}$, $C(O)NR^{33}R^{36}$, $C(S)NR^{33}R^{36}$, $C(=NR^{36})SR^{37}$ or $C(=NR^{36})OR^{37}$, $R^{31}$ and $R^{33}$ each independently represents an optionally substituted hydrocarbyl, perhalogenated hydrocarbyl or an optionally substituted heterocyclyl group, and $R^{36}$ and $R^{37}$ are each independently hydrogen or a group as defined for $R^{33}$;

E represents a linking group;

M represents a metal capable of catalysing transfer hydrogenation; and

Y represents an anionic group, a basic ligand or a vacant site;

provided that when Y is not a vacant site that at least one of A or B carries a hydrogen atom.

The catalytic species is believed to be substantially as represented in the above formula. It may be introduced on a solid support.

Optionally substituted hydrocarbyl, perhalogenated hydrocarbyl or optionally substituted heterocyclyl groups which may be represented by $R^{29-31}$ or $R^{33-35}$ are as defined hereinbefore for $R^5$.

The neutral optionally substituted hydrocarbyl or perhalogenated hydrocarbyl ligand which may be represented by $R^{27}$ includes optionally substituted aryl and alkenyl ligands.

Optionally substituted aryl ligands which may be represented by $R^{27}$ may contain 1 ring or 2 or more fused rings which include cycloalkyl, aryl or heterocyclic rings. Preferably, the ligand comprises a 6 membered aromatic ring. The ring or rings of the aryl ligand are often substituted with hydrocarbyl groups. The substitution pattern and the number of substituents will vary and may be influenced by the number of rings present, but often from 1 to 6 hydrocarbyl substituent groups are present, preferably 2, 3 or 6 hydrocarbyl groups and more preferably 6 hydrocarbyl groups. Preferred hydrocarbyl substituents include methyl, ethyl, iso-propyl, menthyl, neomenthyl and phenyl. Particularly when the aryl ligand is a single ring, the ligand is preferably benzene or a substituted benzene. When the ligand is a perhalogenated hydrocarbyl, preferably it is a polyhalogenated benzene such as hexachlorobenzene or hexafluorobenzne. When the hydrocarbyl substitutents contain enantiomeric and/or diastereomeric centres, it is preferred that the enantiomerically and/or diastereomerically purified forms of these are used. Benzene, p-cymyl, mesitylene and hexamethylbenzene are especially preferred ligands.

Optionally substituted alkenyl ligands which may be represented by $R^{27}$ include $C_{2-30}$, and preferably $C_{6-12}$, alkenes or cycloalkenes with preferably two or more carbon-carbon double bonds, preferably only two carbon-carbon double bonds. The carbon-carbon double bonds may optionally be conjugated to other unsaturated systems which may be present, but are preferably conjugated to each other. The alkenes or cycloalkenes may be substituted preferably with hydrocarbyl substituents. When the alkene has only one double bond, the optionally substituted alkenyl ligand may comprise two separate alkenes. Preferred hydrocarbyl substituents include methyl, ethyl, iso-propyl and phenyl. Examples of optionally substituted alkenyl ligands include cyclo-octa-1,5-diene and 2,5-norbornadiene. Cyclo-octa-1,5-diene is especially preferred.

Optionally substituted cyclopentadienyl groups which may be represented by $R^{27}$ includes cyclopentadienyl groups capable of eta-5 bonding. The cyclopentadienyl group is often substituted with from 1 to 5 hydrocarbyl groups, preferably with 3 to 5 hydrocarbyl groups and more preferably with 5 hydrocarbyl groups. Preferred hydrocarbyl substituents include methyl, ethyl and phenyl. When the hydrocarbyl substitutents contain enantiomeric and/or diastereomeric centres, it is preferred that the enantiomerically and/or diastereomerically purified forms of these are used. Examples of optionally substituted cyclopentadienyl groups include cyclopentadienyl, pentamethyl-cyclopentadienyl, pentaphenylcyclopentadienyl, tetraphenylcyclopentadienyl, ethyltetramethylpentadienyl, menthyltetraphenylcyclopentadienyl, neomenthyl-tetraphenylcyclopentadienyl, menthylcyclopentadienyl, neomenthylcyclopentadienyl, tetrahydroindenyl, menthyltetrahydroindenyl and neomenthyltetrahydroindenyl groups. Pentamethylcyclopentadienyl is especially preferred.

When either A or B is an amide group represented by $-NR^{28}-$, $-NHR^{28}$, $NR^{28}R^{29}$, $-NR^{32}-$, $-NHR^{32}$ or $NR^{31}R^{32}$ wherein $R^{29}$ and $R^{31}$ are as hereinbefore defined, and where $R^{28}$ or $R^{32}$ is an acyl group represented by $-C(O)R^{30}$ or $-C(O)R^{33}$, $R^{30}$ and $R^{33}$ independently are often linear or branched $C_{1-7}$alkyl, $C_{1-8}$-cycloalkyl or aryl, for example phenyl. Examples of acyl groups which may be represented by $R^{28}$ or $R^{33}$ include benzoyl, acetyl and halogenoacetyl, especially trifluoroacetyl, groups.

When either A or B is present as a sulphonamide group represented by $-NR^{28}-$, $-NHR^{28}$, $NR^{28}R^{29}$, $-NR^{32}-$, $-NHR^{32}$ or $NR^{31}R^{32}$ wherein $R^{29}$ and $R^{31}$ are as hereinbefore defined, and where $R^{28}$ or $R^{32}$ is a sulphonyl group represented by $-S(O)_2R^{30}$ or $-S(O)_2R^{33}$, $R^{30}$ and $R^{33}$ independently are often linear or branched $C_{1-8}$alkyl, $C_{1-8}$cycloalkyl or aryl, for example phenyl. Preferred sulphonyl groups include methanesulphonyl, trifluoromethanesulphonyl and especially p-toluenesulphonyl groups and naphthylsulphonyl groups.

When either of A or B is present as a group represented by $-NR^{28}-$, $-NHR^{28}$, $NR^{28}R^{29}$, $-NR^{32}-$, $-NHR^{32}$ or $NR^{31}R^{32}$ wherein $R^{29}$ and $R^{31}$ are as hereinbefore defined, and where $R^{28}$ or $R^{32}$ is a group represented by $C(O)NR^{30}R^{34}$, $C(S)NR^{30}R^{34}$, $C(=NR^{34})SR^{35}$, $C(=NR^{34})OR^{35}$, $C(O)NR^{33}R^{36}$, $C(S)NR^{33}R^{36}$, $C(=NR^{36})SR^{37}$ or C(=NR³⁶)OR³⁷, R³⁰ and R³³ independently are often linear or branched C₁₋₈alkyl, such as methyl, ethyl, isopropyl, C₁₋₈cycloalkyl or aryl, for example phenyl, groups and R³⁴⁻³⁷ are often each independently hydrogen or linear or branched C₁₋₈alkyl, such as methyl, ethyl, isopropyl, C₁₋₈cycloalkyl or aryl, for example phenyl, groups.

When B is present as a group represented by —OR³¹, —SR³¹, —PR³¹— or —PR³¹R³³, R³¹ and R³³ independently are often linear or branched C₁₋₄alkyl, such as methyl, ethyl, isopropyl, C₁₋₈cycloalkyl or aryl, for example phenyl.

It will be recognised that the precise nature of A and B will be determined by whether A and/or B are formally bonded to the metal or are coordinated to the metal via a lone pair of electrons.

The groups A and B are connected by a linking group E. The linking group E achieves a suitable conformation of A and B so as to allow both A and B to bond or coordinate to the metal, M. A and B are commonly linked through 2, 3 or 4 atoms. The atoms in E linking A and B may carry one or more substituents. The atoms in E, especially the atoms alpha to A or B, may be linked to A and B, in such a way as to form a heterocyclic ring, preferably a saturated ring, and particularly a 5, 6 or 7-membered ring. Such a ring may be fused to one or more other rings. Often the atoms linking A and B will be carbon atoms. Preferably, one or more of the carbon atoms linking A and B will carry substituents in addition to A or B. Substituent groups include those which may substitute R¹, as defined above. Advantageously, any such substituent groups are selected to be groups which do not coordinate with the metal, M. Preferred substituents include halogen, cyano, nitro, sulphonyl, hydrocarbyl, perhalogenated hydrocarbyl and heterocyclyl groups as defined above. Most preferred substituents are C₁₋₆ alkyl groups, and phenyl groups. Most preferably, A and B are linked by two carbon atoms, and especially an optionally substituted ethyl moiety. When A and B are linked by two carbon atoms, the two carbon atoms linking A and B may comprise part of an aromatic or aliphatic cyclic group, particularly a 5, 6 or 7-membered ring. Such a ring may be fused to one or more other such rings. Particularly preferred are embodiments in which E represents a 2 carbon atom separation and one or both of the carbon atoms carries an optionally substituted aryl group as defined above or E represents a 2 carbon atom separation which comprises a cyclopentane or cyclohexane ring, optionally fused to a phenyl ring.

E preferably comprises part of a compound having at least one stereospecific centre. Where any or all of the 2, 3 or 4 atoms linking A and B are substituted so as to define at least one stereospecific centre on one or more of these atoms, it is preferred that at least one of the stereospecific centres be located at the atom adjacent to either group A or B. When at least one such stereospecific centre is present, it is advantageously present in an enantiomerically purified state.

When B represents —O— or —OH, and the adjacent atom in E is carbon, it is preferred that B does not form part of a carboxylic group.

Compounds which may be represented by A-E-B, or from which A-E-B may be derived by deprotonation, are often aminoalcohols, including 4-aminoalkan-1-ols, 1-aminoalkan-4-ols, 3-aminoalkan-1-ols, 1-aminoalkan-3-ols, and especially 2-aminoalkan-1-ols, 1-aminoalkan-2-ols, 3-aminoalkan-2-ols and 2-aminoalkan-3-ols, and particularly 2-aminoethanols or 3-aminopropanols, or are diamines, including 1,4-diaminoalkanes, 1,3-diaminoalkanes, especially 1,2- or 2,3-diaminoalkanes and particularly ethylenediamines. Further aminoalcohols that may be represented by A-E-B are 2-aminocyclopentanols and 2-aminocyclohexanols, preferably fused to a phenyl ring. Further diamines that may be represented by A-E-B are 1,2-diaminocyclopentanes and 1,2-diaminocyclohexanes, preferably fused to a phenyl ring. The amino groups may advantageously be N-tosylated. When a diaimine is represented by A-E-B, preferably at least one amino group is N-tosylated. The aminoalcohols or diamines are advantageously substituted, especially on the linking group, E, by at least one alkyl group, such as a C₁₋₄-alkyl, and particularly a methyl, group or at least one aryl group, particularly a phenyl group.

Specific examples of compounds which can be represented by A-E-B and the protonated equivalents from which they may be derived are:

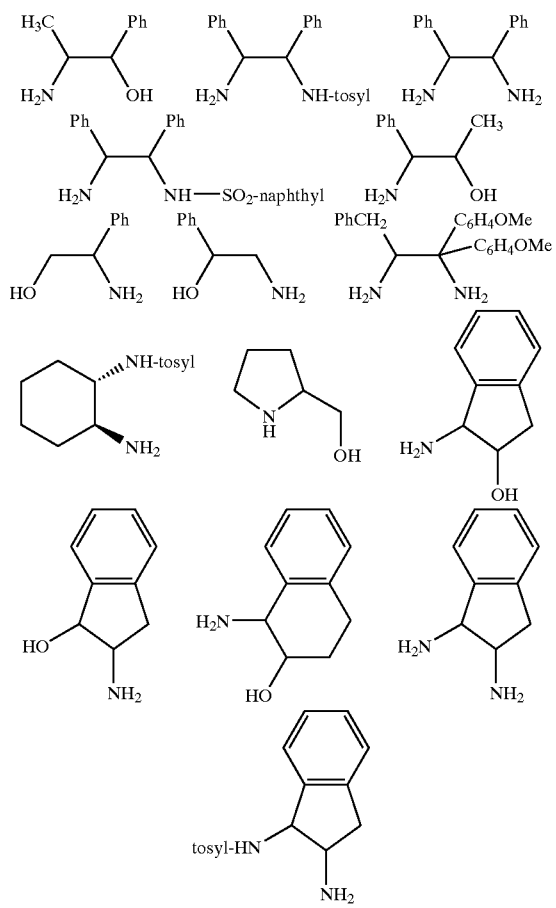

Preferably, the enantiomerically and/or diastereomerically purified forms of these are used. Examples include (1S,2R)-(+)-norephedrine, (1R,2S)-(+)-cis-1-amino-2-indanol, (1S,2R)-2-amino-1,2-diphenylethanol, (1S,2R)-(−)-cis-1-amino-2-indanol, (1R,2S)-(−)-norephedrine, (S)-(+)-2-amino-1-phenylethanol, (1R,2S)-2-amino-1,2-diphenylethanol, N-tosyl-(1R,2R)-1,2-diphenylethylenediamine, N-tosyl-(1S,2S)-1,2-diphenylethylenediamine, (1R,2S)-cis-1,2-indandiamine, (1S,2R)-cis-1,2-indandiamine, (R)-(−)-2-pyrrolidinemethanol and (S)-(+)-2-pyrrolidinemethanol.

Metals which may be represented by M include metals which are capable of catalysing transfer hydrogenation. Preferred metals include transition metals, more preferably the metals in Group VIII of the Periodic Table, especially ruthenium, rhodium or iridium. When the metal is ruthenium it is preferably present in valence state II. When the metal is rhodium or iridium it is preferably present in valence state I when $R^{27}$ is a neutral optionally substituted hydrocarbyl or a neutral optionally substituted perhalogenated hydrocarbyl ligand, and preferably present in valence state III when $R^{27}$ is an optionally substituted cyclopentadienyl ligand.

Anionic groups which may be represented by Y include hydride, hydroxy, hydrocarbyloxy, hydrocarbylamino and halogen groups. Preferably when a halogen is represented by Y, the halogen is chloride. When a hydrocarbyloxy or hydrocarbylamino group is represented by Y, the group may be derived from the deprotonation of the hydrogen donor utilised in the reaction.

Basic ligands which may be represented by Y include water, $C_{1-4}$ alcohols, $C_{1-8}$ primary or secondary amines, or the hydrogen donor which is present in the reaction system. A preferred basic ligand represented by Y is water.

Most preferably, the nature of A-E-B, $R^{27}$ and Y are chosen such that the catalyst is chiral. When such is the case, an enantiomerically and/or diastereomerically purified form is preferably employed. Such catalysts are most advantageously employed in asymmetric transfer hydrogenation processes. In many embodiments, the chirality of the catalyst is derived from the nature of A-E-B.

Examples of catalysts which may be employed in the process of the present invention include

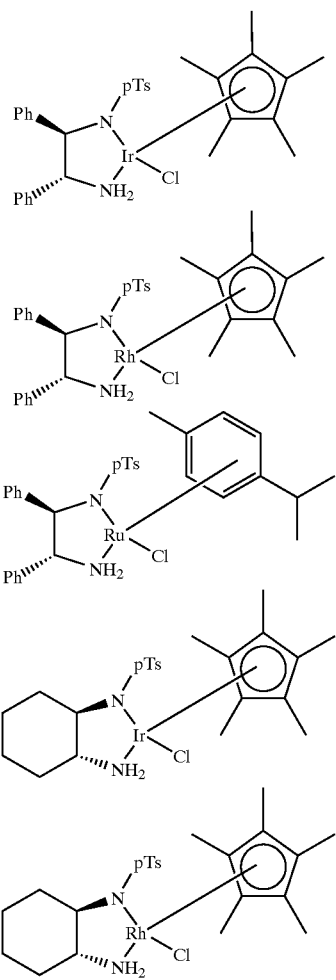

-continued

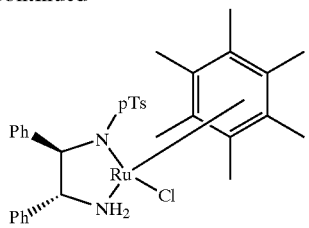

The process is carried out preferably in the presence of a base, especially when Y is not a vacant site. The $pK_a$ of the base is preferably at least 8.0, especially at least 10.0. Convenient bases are the hydroxides, alkoxides and carbonates of alkali metals; tertiary amines and quaternary ammonium compounds. Preferred bases are sodium 2-propoxide and triethylamine. When the hydrogen donor is not an acid, the quantity of base used can be up to 10.0, commonly up to 5.0, often up to 3.0, frequently up to 2.5 and especially in the range 1.0 to 3.5, by moles of the catalyst. When the hydrogen donor is an acid, the catalyst may be contacted with a base prior to the introduction of the hydrogen donor. In such a case, the mole ratio of base to catalyst prior to the introduction of the hydrogen donor is often from 1:1 to 3:1, and preferably about 1:1.

Although gaseous hydrogen may be present, the process is normally operated in the absence of gaseous hydrogen since it appears to be unnecessary.

Advantageously, the process is, carried substantial absence of carbon dioxide.

Preferably, the process is carried out under a substantially inert atmosphere, for example nitrogen or argon.

When the product(s) from dehydrogenation of the hydrogen donor is volatile, for example boils at under 100° C., the removal of this volatile product is preferred. The removal can be accomplished by distillation preferably at less than atmospheric pressure or by use of inert gas sparging. When reduced pressure distillation is employed, the pressure is often no more than 500 mmHg, commonly no more than 200 mmHg, preferably in the range of from 5 to 100 mmHg, and most preferably from 10 to 80 mmHg. When the product(s) from dehydrogenation of the hydrogen donor is a gaseous material, for example when formic acid is present as a hydrogen donor, the removal is most preferably accomplished by the use of inert gas sparging, with for example nitrogen.

Suitably the process is carried out at temperatures in the range of from minus 78 to plus 150° C., preferably from minus 20 to plus 110° C. and more preferably from minus 5 to plus 60° C. The initial concentration of the substrate, a compound of formula (1), is suitably in the range 0.05 to 1.0 and, for convenient larger scale operation, can be for example up to 6.0 more especially 0.25 to 2.0, on a molar basis. The molar ratio of the substrate to catalyst is suitably no less than 50:1 and can be up to 50000:1, preferably between 100:1 and 5000:1 and more preferably between 200:1 and 2000:1. The hydrogen donor is preferably employed in a molar excess over the substrate, especially from 5 to 50 fold or, if convenience permits, greater, for example up to 500 fold. After reaction, the mixture is worked up by standard procedures.

During the reaction a solvent may be present, preferably a polar solvent, for example methanol, ethanol or i-propanol, more preferably a polar aprotic solvent, for example acetonitrile, dimethylformamide or dichloromethane. Conveniently, the hydrogen donor may be the solvent when the hydrogen donor is a liquid at the reaction temperature, or it may be used in combination with other solvents. In certain embodiments it is preferable to use a diluent. Diluents include non-polar solvents such as toluene. Usually it is preferred to operate in substantial absence of water, but water may be present in the reaction. If the hydrogen donor or the reaction solvent is not miscible with water and the desired product is water soluble, it may be desirable to have water present as a second phase extracting the product, pushing the equilibrium and preventing loss of product optical purity as the reaction proceeds. The concentration of substrate may be chosen to optimise reaction time, yield and enantiomeric excess.

The catalytic species is believed to be substantially as represented in the above formula. It may be employed as an oligomer or metathesis product, on a solid support or may be generated in situ.

In certain embodiments it has been found that certain catalysts are preferred for the transfer hydrogenation of imines and iminium salts. Catalysts in which A-E-B is derived from N-tosyldiamines, preferably mono-N-tosyldiamines, particularly mono-N-tosylated ethylenediamines, are preferred. Especially, M is also ruthenium (II) and $R^{27}$ is an aryl group or cyclopentadienyl group, or M is iridium (I) or rhodium (I) and $R^{27}$ is cyclo-octadiene, or M is iridium (III) or rhodium (III) and $R^{27}$ is a cyclopentadienyl group. Further, triethylamine is preferably employed as a base, a mixture of formic acid and triethylamine in the preferred ratio of 5:2 (formic acid:triethylamine) is preferably employed as hydrogen donor. When an iminium salt is present, it is preferably a protonated imine, or is a methylated or benzylated imine with an iodide, formate or trifluoroacetate counter ion. It is believed that when Y is not a vacant site, $R^{27}$ is a neutral ligand and when M is rhodium or iridium and is in valence state (I), A-E-B attaches to M by means of two dative bonds (the lone pairs of the heteroatoms in both A and B coordinate to M). However, when Y is not a vacant site, $R^{27}$ is a cyclopentadienyl ligand and when M is rhodium or iridium and is in valence state (III), A-E-B attaches to M by means of one dative and one formal bond. Whereas when Y is not a vacant site, $R^{27}$ is a neutral ligand and when M is ruthenium and is in valence state (II), A-E-B attaches to M by means of one dative and one formal bond.

The catalyst can be made by reacting a metal aryl, alkenyl or cyclopentadienyl halide complex with a compound of formula A-E-B as defined above or a protonated equivalent from which it may be derived, and, where Y represents a vacant site, reacting the product thereof with a base. The metal aryl or alkenyl halide complex preferably has the formula $[MR^{27}Z_2]_2$ when M is ruthenium (II) and has the formula $[MR^{27}Z]_2$ when M is iridium (I) or rhodium (I), wherein $R^{27}$ is an aryl or alkenyl ligand as defined above, and Z represents a halide, particularly chloride. The metal cyclopentadienyl halide complex preferably has the formula $[MR^{27}Z]_2$ or $[MR^{27}Z]_4$ when M is ruthenium (II) and has the formula $[MR^{27}Z]_2$ when M is iridium (III) or rhodium (III), wherein $R^{27}$ is an optionally substituted cyclopentadienyl ligand as defined above, and Z represents a halide, particularly chloride.

For the preparation of the catalysts according to the present invention, a solvent is preferably present. Suitable reaction temperatures are in the range 0–100, for example 20–70° C., often giving reaction times of 0.5–24.0 h. After reaction is complete, the catalyst may if desired be isolated, but is more conveniently stored as the solution or used soon after preparation. The solution can contain the hydrogen donor and this, if a secondary alcohol, may be present in or used as the solvent for steps (a) and/or (b). The preparation and after-handling should preferably be under an inert atmosphere, and particularly in carbon dioxide and oxygen-free conditions.

The catalyst or catalyst solution is generally treated with base either just prior to use in a transfer hydrogenation reaction, or during use. This can be accomplished by adding base to the catalyst in solution, or to the compound of formula (1) in solution, or by addition to the transfer hydrogenation reaction.

Transfer hydrogenation can be accomplished by transferring the solution of catalyst to a solution of substrate, a compound of general formula I. Alternatively a solution of substrate can be added to a solution of catalyst. Base may be pre-added to the catalyst solution and/or the substrate solution, or can be added later. The hydrogen donor if not already present in the catalyst solution may be added to the substrate solution, or may be added to the reaction mixture.

The imine and iminium salt compounds of formula (1) can generally be obtained by known literature methods. Iminium salts, for example, can be prepared by the quaternisation of imines, such as by treatment of imines with alkylating agents.

N-phosphinyl imines can be synthesised from N-hydroxy imines by treatment with a halophosphine. N-Hydroxy imines being readily available from the corresponding aldehyde or ketone by treatment with hydroxylamine. A similar approach can be used for the synthesis of certain N-sulphonylimines whereby N-hydroxy imines are treated with a halosulphoxyl compound in the presence of a base.

Alternatively, N-phosphinyl imines can be synthesised from aldehydes or ketones by treatment with phosphinic amides in the presence of a condensation reagent, such as titanium tetrachloride, and a base.

Many of the N-phosphinyl, N-sulphonyl, N-sulphoxyl and N-carboxy imines can be synthesised from aldehydes or ketones by treatment with the corresponding phosphinamide, sulphonamide, sulphoxamide or carboxamides under dehydrating conditions, such azeotropic water removal, often carried out in the presence of an acid catalyst, such as p-toluene sulphonic acid or trifluoroacetic acid, or a Lewis acid catalyst, treatments with molar equivalents or excesses of drying agents, for example molecular sieves or magnesium sulphate, or treatments with combined lewis acid and dehydrating agents such as titanium tetrachloride or titanium tetraisopropoxide.

N-Carboxy and N-sulphoxyl imines may also be prepared by reaction of ketones with aza Wittig reagents.

N-Sulphoxyl imines may also be prepared by the reaction of a organometallic derivatives of imines, such as an N-lithiated imine, with chiral sulphoxides such as menthyl p-toluene sulphinate.

N-Silylimines can be prepared form organometallic derivative of silazanes such as lithium di(trimethyl) silazamide, and ketones, or by the reaction of organometallic derivatives of imines, such as an N-lithiated imine, with a halosilane.

Furthermore, either by in situ cleavage of the $R^3$ or $R^4$ groups of the amines produced by the process of first aspect of present invention under the process conditions, or by further treatment by for example acid or base hydrolysis, a ready route to primary and secondary amines can be accessed.

According to a second aspect of the present invention there is provided a process for the production of primary or secondary amines

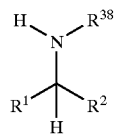

(3)

comprising the steps of
a) generating a substrate of general formula (1) from a carbonyl compound (2),

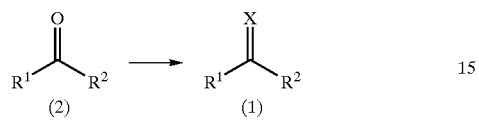

in which X represents $NR^3$ or $(NR^4R^5)^+Q^-$, and $Q^-$ represents a monovalent anion,
b) reacting the substrate of general formula (1) with a hydrogen donor in the presence of a transfer hydrogenation catalyst, and
c) removal of $R^3$ or $R^4$ to give an amine of formula (3)

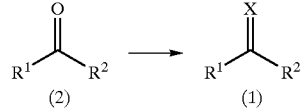

wherein:
$R^1$ and $R^2$ each independently represents a hydrogen atom, an optionally substituted hydrocarbyl, a perhalogenated hydrocarbyl, an optionally substituted heterocyclyl group, a substituted carbonyl functional group, a substituted thiocarbonyl functional group or substituted imino functional group, $R^1$ & $R^2$ optionally being linked in such a way as to form an optionally substituted ring;
$R^3$ and $R^4$ represents —P(O)$R^6R^7$, —P(O)O$R^8$O$R^9$, —P(O)O$R^8$OH, —P(O)(OH)$_2$, —P(O)S$R^{10}$S$R^{11}$, —P(O)S$R^{10}$SH, —P(O)(SH)$_2$, —P(O)N$R^{12}R^{13}$N$R^{14}R^{15}$, —P(O)N$R^{12}R^{13}$NH$R^{14}$, —P(O)NH$R^{12}$NH$R^{14}$, —P(O)N$R^{12}R^{13}$NH$_2$, —P(O)NH$R^{12}$NH$_2$, —P(O)(NH$_2$)$_2$, —P(O)$R^6$O$R^8$, —P(O)$R^6$OH, —P(O)$R^6$S$R^{10}$, —P(O)$R^6$SH, —P(O)$R^6$N$R^{12}R^{13}$, —P(O)$R^6$NH$R^{12}$, —P(O)$R^6$NH$_2$, —P(O)O$R^8$S$R^{10}$, —P(O)O$R^8$SH, —P(O)OHS$R^{10}$, —P(O)OHSH, —P(O)O$R^8$N$R^{12}R^{13}$, —P(O)O$R^8$NH$R^{12}$, —P(O)O$R^8$NH$_2$, —P(O)OHN$R^{12}R^{13}$, —P(O)OHNH$R^{12}$, —P(O)OHNH$_2$, —P(O)S$R^{10}$N$R^{12}R^{13}$, —P(O)S$R^{10}$NH$R^{12}$, —P(O)S$R^{10}$NH$_2$, —P(O)SHN$R^{12}R^{13}$, —P(O)SHNH$R^{12}$, —P(O)SHNH$_2$, —P(S)$R^6R^7$, —P(S)O$R^8$O$R^9$, —P(S)O$R^8$OH, —P(S)(OH)$_2$, —P(S)S$R^{10}$S$R^{11}$, —P(S)S$R^{10}$SH, —P(S)(SH)$_2$, —P(S)N$R^{12}R^{13}$N$R^{14}R^{15}$, —P(S)N$R^{12}R^{13}$NH$R^{14}$, —P(S)NH$R^{12}$NH$R^{14}$, —P(S)N$R^{12}R^{13}$NH$_2$, —P(S)NH$R^{12}$NH$_2$, —P(S)(NH$_2$)$_2$, —P(S)$R^6$O$R^8$, —P(S)$R^6$OH, —P(S)$R^6$S$R^{10}$, —P(S)$R^6$SH, —P(S)$R^6$N$R^{12}R^{13}$, —P(S)$R^6$NH$R^{12}$, —P(S)$R^6$NH$_2$, —P(S)O$R^8$S$R^{10}$, —P(S)OHS$R^{10}$, —P(S)O$R^8$SH, —P(S)OHSH, —P(S)O$R^8$N$R^{12}R^{13}$, —P(S)O$R^8$NH$R^{12}$, —P(S)O$R^8$NH$_2$, —P(S)OHN$R^{12}R^{13}$, —P(S)OHNH$R^{12}$, —P(S)OHNH$_2$, —P(S)S$R^{10}$N$R^{12}R^{13}$,
—P(S)S$R^{10}$NH$R^{12}$, —P(S)S$R^{10}$NH$_2$, —P(S)SHN$R^{12}R^{13}$, —P(S)SHNH$R^{12}$, —P(S)SHNH$_2$, —P$R^6R^7$, —PO$R^8$O$R^9$, —PS$R^{10}$S$R^{11}$, —PN$R^{12}R^{13}$N$R^{14}R^{15}$, —P$R^6$O$R^8$, —P$R^6$S$R^{10}$, —P$R^6$N$R^{12}R^{13}$, —PO$R^8$S$R^{10}$, —PO$R^8$N$R^{12}R^{13}$, —PS$R^{10}$N$R^{12}R^{13}$, —S(O)$R^{16}$, —S(O)$_2R^{17}$, —CO$R^{18}$, —CO$_2R^{19}$, or Si$R^{20}R^{21}R^{22}$;

$R^5$ and $R^{38}$ represents a hydrogen atom, an optionally substituted hydrocarbyl, a perhalogenated hydrocarbyl, or an optionally substituted heterocyclyl group;

$R^6$ and $R^7$ independently represent an optionally substituted hydrocarbyl, a perhalogenated hydrocarbyl, an optionally substituted heterocyclyl group or —N=C$R^{23}R^{24}$ where $R^{23}$ and $R^{24}$ are as defined for $R^1$; and $R^8$ to $R^{22}$ each independently represents an optionally substituted hydrocarbyl, a perhalogenated hydrocarbyl or an optionally substituted heterocyclyl group, one or more of $R^1$ & $R^6$, $R^2$ & $R^7$, $R^6$ & $R^7$, $R^6$ & $R^8$, $R^6$ & $R^{10}$, $R^6$ & $R^{12}$, $R^1$ & $R^8$, $R^2$ & $R^9$, $R^8$ & $R^9$, $R^8$ & $R^{10}$, $R^8$ & $R^{12}$, $R^1$ & $R^{10}$, $R^2$ & $R^{11}$, $R^{10}$ & $R^{11}$, $R^{10}$ & $R^{12}$, $R^1$ & $R^{12}$, $R^2$ & $R^{13}$, $R^{12}$ & $R^{13}$, $R^1$ & $R^{14}$, $R^2$ & $R^{15}$, $R^{14}$ & $R^{15}$, $R^{12}$ & $R^{14}$, $R^1$ & $R^{16}$, $R^1$ & $R^{18}$, $R^1$ & $R^{19}$, $R^1$ & $R^{20}$, $R^2$ & $R^{21}$, $R^{20}$ & $R^{21}$ and $R^{21}$ & $R^{22}$ optionally being linked in such a way as to form an optionally substituted ring(s).

Preferably, when a substrate of formula (1) or an amine of formula (3) comprises one or more optionally substituted ring(s), it is preferred that only one or more of $R^1$ & $R^2$, $R^6$ & $R^7$, $R^8$ & $R^9$, $R^{10}$ & $R^{11}$, $R^{12}$ & $R^{13}$, $R^{14}$ & $R^{15}$, $R^{12}$ & $R^{14}$, $R^{20}$ & $R^{21}$ and $R^{21}$ & $R^{22}$ are optionally linked in such a way as to form an optionally substituted ring(s).

When the substrate of general formula (1) is an imine [i.e. X=$NR^3$], the step of generating the substrate of general formula (1) from a carbonyl compound (2),

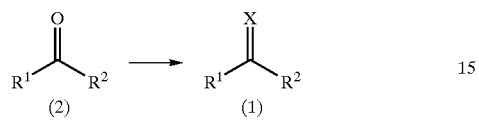

is preferably accomplished by treating a carbonyl compound of formula (2) with a substituted amino compound $R^3NH_2$.

When the substrate of general formula (1) is an iminium salt [i.e. X=$(NR^4R^5)^+Q^-$], the step of generating the substrate of general formula (1) from a carbonyl compound (2),

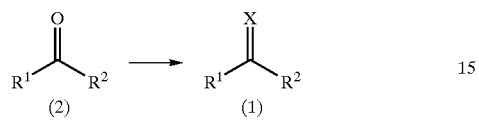

is preferably accomplished by treating a carbonyl compound of formula (2) with a substituted amino compound $R^4NH_2$ and quaternizing or protonating the resulting imine to give the iminium salt.

In certain embodiments, particularly in the generation of imines or iminium salts wherein $R^3$ or $R^4$ contain a phosphorous oxygen double bond, it is preferable in the step of generating the substrate of general formula (1) from a carbonyl compound (2) first to treat the carbonyl compound of formula (2) with hydroxylamine to generate the corresponding oxime, and then to react the oxime with an activated species containing the groups that will form $R^3$ or $R^4$, such as halo derivative, for example ClP(Ph)$_2$.

When reacting the substrate of general formula (1) with a hydrogen donor in the presence of a transfer hydrogenation catalyst to give an amine, the step is carried out in accordance with reference to the first aspect of the present invention as described herein before.

The step of removal of the $R^3$ or $R^4$ may be carried out by any means which is generally known to cleave groups represented by $R^3$ or $R^4$ which are attached to an amine. Preferably, $R^3$ or $R^4$ are removed either by treatment with acid, treatment with base, hydrogenation or treatment with nucleophilic agents, such as fluoride, the method employed being selected according to the nature of $R^3$ or $R^4$.

In many embodiments, $R^3$ or $R^4$, especially when $R^3$ or $R^4$ is a group selected from —$P(O)R^6R^7$, —$P(O)OR^8OR^9$, —$P(O)OR^8OH$, —$P(O)(OH)_2$, —$P(O)SR^{10}SR^{11}$, —$P(O)SR^{10}SH$, —$P(O)(SH)_2$, —$P(O)NR^{12}R^{13}NR^{14}R^{15}$, —$P(O)NR^{12}R^{13}NHR^{14}$, —$P(O)NHR^{12}NHR^{14}$, —$P(O)NR^{12}R^{13}NH_2$, —$P(O)NHR^{12}NH_2$, —$P(O)(NH_2)_2$, —$P(O)R^6OR^8$, —$P(O)R^6OH$, —$P(O)R^6SR^{10}$, —$P(O)R^6SH$, —$P(O)R^6NR^{12}R^{13}$, —$P(O)R^6NHR^{12}$, —$P(O)R^6NH_2$, —$P(O)OR^8SR^{10}$, —$P(O)OR^8SH$, —$P(O)OHSR^{10}$, —$P(O)OHSH$, —$P(O)OR^8NR^{12}R^{13}$, —$P(O)OR^8NHR^{12}$, —$P(O)OR^8NH_2$, —$P(O)OHNR^{12}R^{13}$, —$P(O)OHNHR^{12}$, —$P(O)OHNH_2$, —$P(O)SR^{10}NR^{12}R^{13}$, —$P(O)SR^{10}NHR^{12}$, —$P(O)SR^{10}NH_2$, —$P(O)SHNR^{12}R^{13}$, —$P(O)SHNHR^{12}$, —$P(O)SHNH_2$, —$P(S)R^6R^7$, —$P(S)OR^8OR^9$, —$P(S)OR^8OH$, —$P(S)(OH)_2$, —$P(S)SR^{10}SR^{11}$, —$P(S)SR^{10}SH$, —$P(S)(SH)_2$, —$P(S)NR^{12}R^{13}NR^{14}R^{15}$, —$P(S)NR^{12}R^{13}NHR^{14}$, —$P(S)NHR^{12}NHR^{14}$, —$P(S)NR^{12}R^{13}NH_2$, —$P(S)NHR^{12}NH_2$, —$P(S)(NH_2)_2$, —$P(S)R^6OR^8$, —$P(S)R^6OH$, —$P(S)R^6SR^{10}$, —$P(S)R^6SH$, —$P(S)R^6NR^{12}R^{13}$, —$P(S)R^6NHR^{12}$, —$P(S)R^6NH_2$, —$P(S)OR^8SR^{10}$, —$P(S)OHSR^{10}$, —$P(S)OR^8SH$, —$P(S)OHSH$, —$P(S)OR^8NR^{12}R^{13}$, —$P(S)OR^8NHR^{12}$, —$P(S)OR^8NH_2$, —$P(S)OHNR^{12}R^{13}$, —$P(S)OHNHR^{12}$, —$P(S)OHNH_2$, —$P(S)SR^{10}NR^{12}R^{13}$, —$P(S)SR^{10}NHR^{12}$, —$P(S)SR^{10}NH_2$, —$P(S)SHNR^{12}R^{13}$, —$P(S)SHNHR^{12}$, and —$P(S)SHNH_2$, are removed by treatment with acid, such as gaseous hydrogen chloride, aqueous hydrochloric acid, hydrochloric acid/alcohol mixtures, acetic acid/formic acid/water mixture, trifluoroacetic acid, p-toluenesulphonic acid, or other mineral acids. Preferably, gaseous hydrogen chloride is bubbled through a solution of the phosphorous substituted amine, or the phosphorous substituted amine is treated with an hydrochloric acid solution to effect the cleavage of the nitrogen-phosphorous bond.

When $R^3$ or $R^4$ is a group represented by $CO_2R^{19}$ treatments with acids or reductive methods may be used to remove the $R^3$ or $R^4$ group. When $R^{19}$ is a benzyl group, reductive methods such as hydrogenation in the presence of palladium or charcoal and dissolving metal reductions, or treatment with strong acid, such as hydrogen bromide/acetic acid mixtures, may be employed. When $R^{19}$ is a t-butyl group treatment with an acid such as p-toluenesulphonic or trifluoroacetic acid in an organic solvent such as alcohols, ethers or acetonitrile may be employed. When $R^{19}$ is a methyl group, more forcing conditions may be required such as treatments with hydrazine or alkali metal hydroxides.

When $R^3$ or $R^4$ is a group represented by $COR^{18}$, the $R^3$ or $R^4$ group may be removed by acid or base hydrolysis.

When $R^3$ or $R^4$ is a group represented by —$S(O)_2R^{17}$, treatments with acids or reductive methods may be used to remove the $R^3$ or $R^4$ group. When $R^{17}$ is a methyl group hydride reductions, for example using lithium aluminium hydride, or dissolving metal reductions may be employed. When $R^{17}$ is a p-tolyl group treatment in strong acid, such as trifluoroacetic acid in methanol or 6M hydrocholoric acid, may be employed. When $R^{17}$ is a trimethylsilylethyl group treatment with an alkali metal fluoride, preferably caesium fluoride, may be employed.

When $R^3$ or $R^4$ is a group represented by $SiR^{20}R^{21}R^{22}$, treatments with acids or alkali metal fluorides may be used to remove the $R^3$ or $R^4$ group.

The invention is illustrated by the following Examples.

EXAMPLE 1

Synthesis of Acetonaphthone Oxime

| Reactant | Wt/Vol | Mol. Wt | Mol | Mol ratio |
| --- | --- | --- | --- | --- |
| 1-acetonaphthone | 1 g | 170.2 | 5.9 mmol | 1 |
| hydroxylamine hydrochloride | 0.98 g | 69.5 | 10.0 mmol | 1.7 |
| pyridine | 10 ml | 79.1 | — | — |

In a 50 ml round-bottom flask, a mixture of acetonaphthone, hydroxylamine hydrochloride in pyridine was stirred, at room temperature under nitrogen blanket, for five days. The reaction mixture was then concentrated under vacuum to remove most of pyridine. The oil was then dissolved in dichloromethane. The product precipitated on standing. The product was obtained as a white solid in 65% yield.

Note: after reaction, the compound exhibit a 75/25 E/Z isomers ratio. After precipitation, one single isomer (E) was observed by $^1H$ NMR.

EXAMPLE 2

Synthesis of Acetophenone Oxime

| Reactant | Wt/Vol | Mol. Wt | Mol | Mol ratio |
| --- | --- | --- | --- | --- |
| acetonaphthone | 1 g | 120.1 | 8.3 mmol | 1 |
| hydroxylamine hydrochloride | 0.695 g | 69.5 | 14.1 mmol | 1.7 |
| pyridine | 5 ml | 79.1 | — | — |

In a 50 ml round-bottom flask, a mixture of acetophenone, hydroxylamine hydrochloride in pyridine was stirred, at room temperature under nitrogen blanket, for five days. The reaction mixture was then concentrated under vacuum to remove most of pyridine. The oil was then distilled at 55° C. under 0.1 mbar. The product was obtained in 95% yield.

Note: the isomer E/Z ratio of the isolated compound was 87/13 as measured by $^1H$ NMR.

EXAMPLE 3

Synthesis of 2-Octanone Oxime

| Reactant | Wt/Vol | Mol. Wt | Mol | Mol ratio |
| --- | --- | --- | --- | --- |
| 2-octanone | 1.2 g | 128.2 | 7.8 mmol | 1 |
| hydroxylamine hydrochloride | 0.92 g | 69.5 | 13.3 mmol | 1.7 |
| pyridine | 10 ml | 79.1 | — | — |

In a 50 ml round-bottom flask, a mixture of 2-octanone, hydroxylamine hydrochloride in pyridine was stirred, at room temperature under nitrogen blanket, for five days. The reaction mixture was then concentrated under vacuum to remove most of pyridine. The oil was then dissolved in dichloromethane. The product precipitated on standing. The product was obtained as a white solid in 87% yield.

EXAMPLE 4

Synthesis of N-diphenylphosphinyl-1,1-methylnaphthyl Imine

| Reactant | Wt/Vol | Mol. Wt | Mol | Mol ratio |
|---|---|---|---|---|
| acetonaphthone oxime | 1 g | 185 | 5.4 mmol | 1 |
| triethylamine | 0.75 ml | 101.2 | 5.4 mmol | 1 |
| chlorodiphenylphosphine | 0.97 ml | 220.6 | 5.4 mmol | 1 |
| diethyl ether | 5 ml | 74.1 | — | — |
| dichloromethane | 5 + 2 ml | 84.9 | — | — |

To a stirred solution of acetonapthone oxime and triethylamine in diethyl ether/dichloromethane (1/1:10 ml) was added dropwise a solution of chlorodiphenylphosphine in dichloromethane (2 ml) at −45° C. After addition, the temperature (−45° C.) was maintained for 1 hour and then was allowed to slowly rise to reach room temperature without removing the ice bath (dry ice-acetone). The reaction mixture was stirred at room temperature overnight. The solution was then filtered to remove the triethylamine hydrochloride precipitate and washed with a mixture of diethyl ether/dichloromethane (1/1). The liquid solution was concentrated to give a brown viscous oil in 94% yield. Recrystallisation in toluene/diethyl ether gave the product as yellow crystals.

EXAMPLE 5

Synthesis of N-diphenylphosphinyl-1,1-methylphenyl Imine

| Reactant | Wt/Vol | Mol. Wt | Mol | Mol ratio |
|---|---|---|---|---|
| acetonaphthone oxime | 1.06 g | 135 | 7.8 mmol | 1 |
| triethylamine | 1.1 ml | 101.2 | 7.8 mmol | 1 |
| chlorodiphenylphosphine | 1.4 ml | 220.6 | 7.8 mmol | 1 |
| diethyl ether | 5 ml | 74.1 | — | — |
| dichloromethane | 5 + 2 ml | 84.9 | — | — |

To a stirred solution of acetophenone oxime and triethylamine in diethyl ether/dichloromethane (1/1:10 ml) was added dropwise a solution of chlorodiphenylphosphine in dichloromethane (2 ml) at −45° C. After addition, the temperature (−45° C.) was maintained for 1 hour and then was allowed to slowly rise to reach room temperature without removing the ice bath (dry ice-acetone). The reaction mixture was stirred at room temperature overnight. The solution was then filtered to remove the triethylamine hydro chloride precipitate and washed with a mixture of diethyl ether/dichloromethane (1/1). The product was obtained as a yellow solid in 80% yield after concentration, and was washed with a mixture of diethyl ether/dichloromethane (1/1).

EXAMPLE 6

Synthesis of N-diphenylphosphinyl-1,1-methylhexyl Imine

| Reactant | Wt/Vol | Mol. Wt | Mol | Mol ratio |
|---|---|---|---|---|
| 2-octanone oxime | 0.97 g | 143 | 6.8 mmol | 1 |
| triethylamine | 0.95 ml | 101.2 | 6.8 mmol | 1 |
| chlorodiphenylphosphine | 1.2 ml | 220.6 | 6.8 mmol | 1 |
| diethyl ether | 5 ml | 74.1 | — | — |
| dichloromethane | 5 + 2 ml | 84.9 | — | — |

To a stirred solution of acetophenone oxime and triethylamine in diethyl ether/dichloromethane (1/1:10 ml) was added dropwise a solution of chlorodiphenylphosphine in dichloromethane (2 ml) at 45° C. After addition, the temperature (−45° C.) was maintained for 1 hour and then was allowed to slowly rise to reach room temperature without removing the ice bath (dry ice-acetone). The reaction mixture was stirred at room temperature overnight. The solution was then filtered to remove the triethylamine hydrochloride precipitate and washed with a mixture of diethyl ether/dichloromethane (1/1). The product was obtained as a colourless oil in 84% yield after concentration. Recrystallisation in toluene/diethyl ether gave the product as white crystals.

EXAMPLE 7

Synthesis of N-diethylphosphinyl-1,1methylnaphthyl Imine

| Reactant | Wt/Vol | Mol. Wt | Mol | Mol ratio |
|---|---|---|---|---|
| acetonaphthone oxime | 1 g | 185 | 5.4 mmol | 1 |
| triethylamine | 0.75 ml | 101.2 | 5.4 mmol | 1 |
| chlorodiethylphosphine | 0.66 ml | 124.5 | 5.4 mmol | 1 |
| diethyl ether | 5 ml | 74.1 | — | — |
| dichloromethane | 5 + 2 ml | 84.9 | — | — |

To a stirred solution of acetonapthone oxime and triethylamine in diethyl ether/dichloromethane (1/1:10 ml) was added dropwise a solution of chlorodiethylphosphine in dichloromethane (2 ml) at −45° C. After addition, the temperature (−45° C.) was maintained for 1 hour and then was allowed to slowly rise to reach room temperature without removing the ice bath (dry ice-acetone). The reaction mixture was stirred at room temperature overnight. The solution was then filtered to remove the triethylamine hydrochloride precipitate and washed with a mixture of diethyl ether/dichloromethane (1/1). The product was obtained as a brown oil in 85% yield after concentration. No further purification was made.

EXAMPLE 8

Reduction of N-diphenylphosphinyl-1,1-methylnaphthyl Imine

| Reactant | Wt/Vol | Mol. Wt | Mol | Mol ratio |
|---|---|---|---|---|
| [Rh(Cp*)Cl$_2$]$_2$** | 1.54 mg | 617.8 | 2.5 μmol | 0.5 |
| (R,R)-N-Tosyl-1,2-diamino-1,2-diphenylethane | 1.83 mg | 366 | 5 μmol | 1 |
| Methanol | 1.6 ml | 32 | — | — |
| Et$_3$N/HCO$_2$H [2:5] | 2 ml | 101.2/42 | 24 mmol of HCO$_2$H | 1200 |
| (imine structure) | 369 mg | 369 | 1 mmol | 200 |

Cp* - pentamethylcyclopentadienyl
Notes: **purchased from The Aldrich Chemical Co.
Prior to the reaction, all solvents were degassed, for example:
10 ml of anhydrous methanol was added by syringe to a sealed clean dry round bottomed flask and degassed; either by reducing the pressure until the solvent began to boil and backfilling with nitrogen 3 times, or by bubbling nitrogen through the solution for at least 20 mins.

To a Schlenk flask was added the (R,R)-N-tosyl-1,2-diamino-1,2-diphenylethane, rhodium pentamethylcyclopentadienyl dichloride dimer, N-diphenylphosphinyl-1,1-methylnaphthyl imine and methanol. The flask was stoppered with a 'Suba-seal' (RTM). Its contents were evacuated, then purged at room temperature by 3 changes of nitrogen. To the yellow/orange solution was added the formic acid/triethylamine mixture dropwise. After 30 mins, the solution had changed colour to red/brown. The mixture was stirred for 3 hours while being purged with nitrogen, the reaction was then quenched by the addition of saturated sodium carbonate solution (1 ml). The aqueous solution was then shaken with dichloromethane (5 ml), the organic phase separated and collected. The organic phase was then dried by contacting with solid anhydrous magnesium sulphate and then filtering off the solid, then the solvent was removed in vacuo to give product in >95% conversion and >99% ee. The sample was analysed by $^1$H and $^{31}$P NMR.

EXAMPLE 9

Reduction of N-diphenylphosphinyl-1,1-methylnaphthyl imine with a Rhodium catalyst

| Reactant | Wt/Vol | Mol. Wt | Mol | Mol ratio |
|---|---|---|---|---|
| N-diphenylphosphinyl-1,1-methylnaphthyl imine | 369 mg | 369 | 1 mmol | 50 |
| [RhCp*Cl$_2$]$_2$ | 6.2 mg | 617.8 | 10 μmol | 0.5 |
| (R,R)-N-tosyl-1,2-diamino-1,2-diphenylethane | 7.3 mg | 366 | 20 μmol | 1 |
| acetonitrile | 1.6 ml | 41 | — | — |
| Et$_3$N/HCO$_2$H [2:5] | 2 ml | 101.2/42 | 24 mmol of HCO$_2$H | 1200 |

Cp* = pentamethylcyclopentadienyl

The (R,R)-N-tosyl-1,2-diamino-1,2-diphenylethane and rhodium compound were weighed out into a clean dry Schlenk flask. A solution of N-diphenylphosphinyl-1,1-methylnaphthyl imine in acetonitrile was added. The flask was stoppered with a "Suba-seal" (RTM). The reaction mixture was stirred rapidly and purged at room temperature by 3 changes of nitrogen. After 10 mins, the mixture of triethylamine/formic acid was added dropwise. The orange solution became red/browri. After 3 hours, the reaction mixture was quenched with a saturated solution of Na$_2$CO$_3$ (2 ml). Extraction was then carried out by treatment with dichloromethane (5 ml). The organic layer was dried over magnesium sulphate and concentrated to give the product as a brown oil, in >95% conversion and >99% ee.

Note: the reaction can be carried out with or without a nitrogen purge. The ee were determined by HPLC on a chiral phase column or by $^{31}$P NMR with a chiral shift reagent.

EXAMPLE 10

Reduction of N-diphenylphosphinyl-1,1-methylphenyl imine with a rhodium catalyst

| Reactant | Wt/Vol | Mol. Wt | Mol | Mol ratio |
|---|---|---|---|---|
| N-diphenylphosphinyl-1,1-methylphenyl imine | 319 mg | 319 | 1 mmol | 50 |
| [RhCp*Cl$_2$]$_2$ | 6.2 mg | 617.8 | 10 μmol | 0.5 |
| (R,R)-N-tosyl-1,2-diamino-1,2-diphenylethane | 7.3 mg | 366 | 20 μmol | 1 |
| acetonitrile | 1.6 ml | 41 | — | — |
| Et$_3$N/HCO$_2$H [2:5] | 2 ml | 101.2/42 | 24 mmol of HCO$_2$H | 1200 |

Cp* = pentamethylcyclopentadienyl

The (R,R)-N-tosyl-1,2-diamino-1,2-diphenylethane and rhodium compound were weighed out into a clean dry Schlenk flask. A solution of N-diphenylphosphinyl-1,1-methylphenyl imine in acetonitrile was added. The flask was stoppered with a "Suba-seal" (RTM). The reaction mixture was stirred rapidly and purged at room temperature by 3 changes of nitrogen. After 10 mins, the mixture of triethylamine/formic acid was added dropwise. The yellow solution became red/brown. After 3 hours, the reaction mixture was quenched with a saturated solution of sodium carbonate (2 ml). Extraction was then carried out by treatment with dichloromethane (5 ml). The organic layer was dried over magnesium sulphate and concentrated to give the product as a brown liquid, in >95% conversion and 86% ee.

Note: The ee were determined by HPLC on a chiral phase column or by $^{31}$P NMR with a chiral shift reagent.

EXAMPLE 11

Reduction of N-diphenylphosphinyl-1,1-methylhexyl imine with an Iridium catalyst

| Reactant | Wt/Vol | Mol. Wt | Mol | Mol ratio |
|---|---|---|---|---|
| N-diphenylphosphinyl-1,1-methylhexyl imine | 327 mg | 327 | 1 mmol | 50 |
| [IrCp*Cl$_2$]$_2$ | 7.9 mg | 796.6 | 10 µmol | 0.5 |
| (R,R)-N-tosyl-1,2-diamino-1,2-diphenylethane | 7.3 mg | 366 | 20 µmol | 1 |
| acetonitrile | 1.6 ml | 41 | — | — |
| Et$_3$N/HCO$_2$H [2:5] | 2 ml | 101.2/42 | 24 mmol of HCO$_2$H | 1200 |

Cp* = pentamethylcyclopentadienyl

The (R,R)-N-tosyl-1,2-diamino-1,2-diphenylethane and iridium compound were weighed out into a clean dry Schlenk flask. A solution of N-diphenylphosphinyl-1,1-methylhexyl imine in acetonitrile was added. The flask was stoppered with a "Suba-seal" (RTM). The reaction mixture was stirred rapidly and purged at room temperature by 3 changes of nitrogen. After 10 mins, the mixture of triethylamine/formic acid was added dropwise. The yellow solution became green. After 2 hours, the reaction mixture was quenched with a saturated solution of sodium carbonate (2 ml). Extraction was then carried out by treatment with dichloromethane (5 ml). The organic layer was dried over magnesium sulphate and concentrated to give the product as a brown liquid, in >95% conversion and 95% ee.

Note: The ee were determined by HPLC on a chiral phase column or by $^{31}$P NMR with a chiral shift reagent.

EXAMPLE 12

Reduction of N-diethylphosphinyl-1,1-methylnaphthyl imine with a ruthenium catalyst

| Reactant | Wt/Vol | Mol. Wt | Mol | Mol ratio |
|---|---|---|---|---|
| N-diphenylphosphinyl-1,1-methylnaphthyl imine | 369 mg | 369 | 1 mmol | 50 |
| p-cymeneruthenium-chloride dimer | 6.1 mg | 612.4 | 10 µmol | 0.5 |
| (R,R)-N-tosyl-1,2-diamino-1,2-diphenylethane | 7.3 mg | 366 | 20 µmol | 1 |
| acetonitrile | 1.6 ml | 41 | — | — |
| Et$_3$N/HCO$_2$H [2:5] | 2 ml | 101.2/42 | 24 mmol of HCO$_2$H | 1200 |

The (R,R)-N-tosyl-1,2-diamino-1,2-diphenylethane and ruthenium compound were weighed out into a clean dry Schlenk flask. A solution of N-diethylphosphinyl-1,1-methylnaphthyl imine in acetonitrile was added. The flask was stoppered with a "Suba-seal" (RTM). The reaction mixture was stirred rapidly and purged at room temperature by 3 changes of nitrogen. After 10 mins, the mixture of triethylamine/formic acid was added dropwise. After 2 hours, the reaction mixture was quenched with a saturated solution of sodium carbonate (2 ml). Extraction was then carried out by treatment with dichloromethane (5 ml). The organic layer was dried over magnesium sulphate and concentrated to give the product as a brown oil, in >95% conversion and 84% ee.

Note: The ee were determined by HPLC on a chiral phase column or by $^{31}$P NMR with a chiral shift reagent.

EXAMPLE 13

Reduction of N-diphenylphosphinyl-1,1-methylnaphthyl imine with a Rhodium catalyst

| Reactant | Wt/Vol | Mol. Wt | Mol | Mol ratio |
|---|---|---|---|---|
| N-diphenylphosphinyl-1,1-methylnaphthyl imine | 369 mg | 369 | 1 mmol | 50 |
| [RhCp*Cl$_2$]$_2$ | 6.2 mg | 617.8 | 10 µmol | 0.5 |
| (R,R)-N-tosyl-1,2-diamino-1,2-diphenylethane | 7.3 mg | 366 | 20 µmol | 1 |
| methanol | 1.6 ml | 32 | — | — |
| Et$_3$N/HCO$_2$H [2:5] | 2 ml | 101.2/42 | 24 mmol of HCO$_2$H | 1200 |

Cp* = pentamethylcyclopentadienyl

The (R,R)-N-tosyl-1,2-diamino-1,2-diphenylethane and rhodium compound were weighed out into a clean dry Schlenk flask. The solution of -diphenylphosphinyl-1,1-methylnaphthyl imine in methanol was added. The flask was stoppered with a "Suba-seal" (RTM). The reaction mixture was stirred rapidly and purged at room temperature by 3 changes of nitrogen. After 10 mins, the mixture of triethylamine/formic acid was added dropwise. The yellow/orange solution became red/brown. After 3 hours, the reaction mixture was quenched with a saturated solution of sodium carbonate (2 ml). Extraction was then carried out by treatment with dichloromethane (5 ml). The organic layer was dried over magnesium sulphate and concentrated to give the product as a brown oil, in >95% conversion and >99% ee.

EXAMPLE 14

Reduction of N-diphenylphosphinyl-1,1-methylnaphthyl imine with a Rhodium catalyst

| Reactant | Wt/Vol | Mol. Wt | Mol | Mol ratio |
|---|---|---|---|---|
| N-diphenylphosphinyl-1,1-methylnaphthyl imine | 369 mg | 369 | 1 mmol | 50 |
| [RhCp*Cl$_2$]$_2$ | 6.2 mg | 617.8 | 10 µmol | 0.5 |
| (S,S)-N-tosyl-1,2-diamino-1,2-diphenylethane | 7.3 mg | 366 | 20 µmol | 1 |
| acetonitrile | 1.6 ml | 41 | — | — |
| Et$_3$N/HCO$_2$H [2:5] | 2 ml | 101.2/42 | 24 mmol of HCO$_2$H | 1200 |

Cp* = pentamethylcyclopentadienyl

The (S,S)-N-tosyl-1,2-diamino-1,2-diphenylethane and rhodium compound were weighed out into a clean dry Schlenk flask. The solution of N-diphenylphosphinyl-1,1-methylnaphthyl imine in acetonitrile was added. The flask was stoppered with a "Suba-seal" (RTM). The reaction mixture was stirred rapidly and purged at room temperature by 3 changes of nitrogen. After 10 mins, the mixture of triethylamine/formic acid was added dropwise. The orange solution became red/brown. After 3 hours, the reaction mixture was quenched with a saturated solution of sodium carbonate (2 ml). Extraction was then carried out by treatment with dichloromethane (5 ml). The organic layer was dried over magnesium sulphate and concentrated to give the product as a brown oil, in >95% conversion and >99% ee.

EXAMPLE 15

Reduction of N-diphenylphosphinyl-1,1-methylnaphthyl imine with a Rhodium catalyst

| Reactant | Wt/Vol | Mol. Wt | Mol | Mol ratio |
|---|---|---|---|---|
| N-diphenylphosphinyl-1,1-methylnaphthyl imine | 369 mg | 369 | 1 mmol | 200 |
| [RhCp*Cl$_2$]$_2$ | 1.5 mg | 617.8 | 2.5 µmol | 0.5 |
| (R,R)-N-tosyl-1,2-diamino-1,2-diphenylethane | 1.8 mg | 366 | 5 µmol | 1 |
| acetonitrile | 1.6 ml | 41 | — | — |
| Et$_3$N/HCO$_2$H [2:5] | 2 ml | 101.2/42 | 24 mmol of HCO$_2$H | 4800 |

Cp* = pentamethylcyclopentadienyl

The (R,R)-N-tosyl-1,2-diamino-1,2-diphenylethane and rhodium compound were weighed out into a clean dry Schlenk flask. The solution of N-diphenylphosphinyl-1,1-methylnaphthyl imine in acetonitrile was added. The flask was stoppered with a "Suba-seal" (RTM). The reaction mixture was stirred rapidly and purged at room temperature by 3 changes of nitrogen. After 10 mins, the mixture of Et$_3$N/HCO$_2$H was added dropwise. The orange solution became red/brown. After 3 hours, the reaction mixture was quenched with a saturated solution of sodium carbonate (2 ml). Extraction was then carried out by treatment with dichloromethane (5 ml). The organic layer was dried over magnesium sulphate and concentrated to give the product as a brown oil, in >95% conversion and >99% ee.

EXAMPLE 16

Reduction of N-diphenylphosphinyl-1,1-methylnaphthyl imine with a Rhodium catalyst

| Reactant | Wt/Vol | Mol. Wt | Mol | Mol ratio |
|---|---|---|---|---|
| N-diphenylphosphinyl-1,1-methylnaphthyl imine | 369 mg | 369 | 1 mmol | 50 |
| [RhCp*Cl$_2$]$_2$ | 6.2 mg | 617.8 | 10 µmol | 0.5 |
| (R,R)-N-tosyl-1,2-diamino-1,2-diphenylethane | 7.3 mg | 366 | 20 µmol | 1 |
| acetonitrile | 1.6 ml | 41 | — | — |
| HCO$_2$H | 1 ml | 42 | 24 mmol of HCO$_2$H | 1200 |

Cp* = pentamethylcyclopentadienyl

The (R,R)-N-tosyl-1,2-diamino-1,2-diphenylethane and rhodium compound were weighed out into a clean dry Schlenk flask. The solution N-diphenylphosphinyl-1,1-methylnaphthyl imine in acetonitrile was added. The flask was stoppered with a "Suba-seal" (RTM). The reaction mixture was stirred rapidly and purged at room temperature by 3 changes of nitrogen. After 10 mins, formic acid (1 ml) was added dropwise. The orange solution became brown. After 2 hours, the reaction mixture was quenched with a saturated solution of sodium carbonate (5 ml). Extraction was then carried out by treatment with dichloromethane (5 ml). The organic layer was dried over magnesium sulphate and concentrated to give the product as a brown oil, in >95% conversion and >99% ee.

EXAMPLE 17

Synthesis of 1-Naphthylethylamine

| Reactant | Wt/Vol | Mol. Wt | Mol | Mol ratio |
|---|---|---|---|---|
| N-diphenylphosphinyl-1-naphthylethylamine | 0.2 g | 371 | 0.54 mmol | 1 |
| gaseous hydrogen chloride | — | 36.5 | — | — |
| ethyl alcohol | 10 ml | 46 | — | — |

Gaseous hydrogen chloride was bubbled through a stirred solution of N-diphenylphosphinyl-1-naphthylethylamine in ethyl alcohol for 2 hours at room temperature. The reaction mixture was concentrated, made basic by the addition of an aqueous solution of sodium hydroxide (2 M) and extracted with dichloromethane (3×10 ml). The organic layer was washed with brine (1×10 ml), dried over magnesium sulphate and concentrated to give the product as a yellow liquid in 80% yield.

EXAMPLE 18

Synthesis of 1-phenylethylamine

| Reactant | Wt/Vol | Mol. Wt | Mol | Mol ratio |
|---|---|---|---|---|
| N-diphenylphosphinyl-1-phenylethylamine | 0.2 g | 321 | 0.62 mmol | 1 |
| gaseous hydrogen chloride | — | 36.5 | — | — |
| ethyl alcohol | 10 ml | 46 | — | — |

Gaseous hydrogen chloride was bubbled through a stirred solution of N-diphenylphosphinyl-1-phenylethylamine in ethyl alcohol for 2 hours at room temperature. The reaction mixture was concentrated, made basic by the addition of an aqueous solution of sodium hydroxide (2 M) and extracted with dichloromethane (3×10 ml). The organic layer was washed with brine (1×10 ml), dried over magnesium sulphate and concentrated to give the product as a yellow liquid in 88% yield.

EXAMPLE 19

Synthesis of 1-methylheptylamine

| Reactant | Wt/Vol | Mol. Wt | Mol | Mol ratio |
|---|---|---|---|---|
| N-diphenylphosphinyl-1-methylheptylamine | 0.2 g | 329 | 0.61 mmol | 1 |
| gaseous hydrogen chloride | — | 36.5 | — | — |
| ethyl alcohol | 10 ml | 46 | — | — |

Gaseous hydrogen chloride was bubbled through a stirred solution of N-diphenylphosphinyl-1-methylheptylamine in ethyl alcohol, for 2 hours at room temperature. The reaction mixture was concentrated, made basic by the addition of an aqueous solution of sodium hydroxide (2 M) and extracted with dichloromethane (3×10 ml). The organic layer was washed with brine (1×10 ml), dried over magnesium sulphate and concentrated to give the product as a yellow liquid in 69% yield.

EXAMPLE 20

Synthesis of 1-naphthylethylamine

| Reactant | Wt/Vol | Mol. Wt | Mol | Mol ratio |
|---|---|---|---|---|
| N-diethylphosphinyl-1-naphthylethylamine | 0.2 g | 275 | 0.73 mmol | 1 |
| gaseous hydrogen chloride | — | 36.5 | — | — |
| ethyl alcohol | 10 ml | 46 | — | — |

Gaseous hydrogen chloride was bubbled through a stirred solution of N-diethylphosphinyl-1-naphthylethylamine in ethyl alcohol for 2 hours at room temperature. The reaction mixture was concentrated, made basic by the addition of an aqueous solution of sodium hydroxide (2 M) and extracted with dichloromethane (3×10 ml). The organic layer was washed with brine (1×10 ml), dried over magnesium sulphate and concentrated to give the product as a yellow liquid in 72% yield.

What is claimed is:

1. A process for the transfer hydrogenation of a substrate wherein the substrate is reacted with a hydrogen donor in the presence of a transfer hydrogenation catalyst, wherein the substrate has the general formula

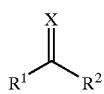

(1)

wherein:

X represents $NR^3$ or $(NR^4R^5)^+Q^-$;

$Q^-$ represents a monovalent anion;

$R^1$ and $R^2$ each independently represents a hydrogen atom, an optionally substituted hydrocarbyl, a perhalogenated hydrocarbyl, an optionally substituted heterocyclyl group, a substituted carbonyl functional group, a substituted thiocarbonyl functional group or substituted imino functional group, $R^1$ & $R^2$ optionally being linked in such a way as to form an optionally substituted ring;

$R^3$ and $R^4$ represents —P(O)$R^6R^7$, —P(O)O$R^8$O$R^9$, —P(O)OR$^8$OH, —P(O)(OH)$_2$, (OH)$_2$, —P(O)SR$^{10}$SR$^{11}$, —P(O)SR$^{10}$SH, —P(O)(SH)$_2$, —P(O)NR$^{12}$R$^{13}$NR$^{14}$R$^{15}$, —P(O)NR$^{12}$R$^{13}$NHR$^{14}$, —P(O)NHR$^{12}$NHR$^{14}$, —P(O)NR$^{12}$R$^{13}$NH$_2$, —P(O)NHR$^{12}$NH$_2$, —P(O)(NH$_2$)$_2$, —P(O)R$^6$OR$^8$, —P(O)R$^6$OH, —P(O)R$^6$SR$^{10}$, —P(O)R$^6$SH, —P(O)R$^6$NR$^{12}$R$^{13}$, —P(O)R$^6$NHR$^{12}$, —P(O)R$^6$NH$_2$, —P(O)OR$^8$SR$^{10}$, —P(O)OR$^8$SH, —P(O)OHSR$^{10}$, —P(O)OHSH, —P(O)OR$^8$NR$^{12}$R$^{13}$, —P(O)OR$^8$NHR$^{12}$, —P(O)OR$^8$N$_2$, —P(O)OHNR$^{12}$R$^{13}$, —P(O)OHNHR$^{12}$, —P(O)OHNH$_2$, —P(O)SR$^{10}$NR$^{12}$R$^{13}$, —P(O)SR$^{10}$NHR$^{12}$, —P(O)SR$^{10}$NH$_2$, —P(O)SHNR$^{12}$R$^{13}$, —P(O)SHNHR$^{12}$, —P(O)SHNH$_2$, —P(S)R$^6$R$^7$, —P(S)OR$^8$OR$^9$, —P(S)OR$^8$OH, —P(S)(OH)$_2$, —P(S)SR$^{10}$SR$^{11}$, —P(S)SR$^{10}$SH, —P(S)(SH)$_2$, —P(S)NR$^{12}$R$^{13}$NR$^{14}$R$^{15}$, —P(S)NR$^{12}$R$^{13}$NHR$^{14}$, —P(S)NHR$^{12}$NHR$^{14}$, —P(S)NR$^{12}$R$^{13}$NH$_2$, —P(S)NHR$^{12}$NH$_2$, —P(S)(NH$_2$)$_2$, —P(S)R$^6$OR$^8$, —P(S)R$^6$OH, —P(S)R$^6$SR$^{10}$, —P(S)R$^6$SH, —P(S)R$^6$NR$^{12}$R$^{13}$, —P(S)R$^6$HR$^{12}$, —P(S)R$^6$NH$_2$, —P(S)OR$^8$SR$^{10}$, —P(S)OHSR$^{10}$, —P(S)OR$^8$SH, —P(S)OHSH, —P(S)OR$^8$NR$^{12}$R$^{13}$, —P(S)OR$^8$NHR$^{12}$, —P(S)OR$^8$NH$_2$, —P(S)OHNR$^{12}$R$^{13}$, —P(S)OHNHR$^{12}$, —P(S)OHNH$_2$, —P(S)SR$^{10}$NR$^{12}$R$^{13}$, —P(S)SR$^{10}$NHR$^{12}$, —P(S)SR$^{10}$NH$_2$, —P(S)SHNR$^{12}$R$^{13}$, —P(S)SHNHR$^{12}$, —P(S)SHNH$_2$, —PR$^6$R$^7$, —POR$^8$OR$^9$, —PSR$^{10}$SR$^{11}$, —PNR$^{12}$R$^{13}$NR$^{14}$R$^{15}$, —PR$^6$OR$^8$, —PR$^6$SR$^{10}$, —PR$^6$NR$^{12}$R$^{13}$, —POR$^8$SR$^{10}$, —POR$^8$NR$^{12}$R$^{13}$, —PSR$^{10}$NR$^{12}$R$^{13}$, —S(O)R$^{16}$, —S(O)$_2$R$^{17}$, —COR$^{18}$, —CO$_2$R$^{19}$, or SiR$^{20}$R$^{21}$R$^{22}$;

$R^5$ represents a hydrogen atom, an optionally substituted hydrocarbyl, a perhalogenated hydrocarbyl, or an optionally substituted heterocyclyl group;

$R^6$ and $R^7$ independently represent an optionally substituted hydrocarbyl, a perhalogenated hydrocarbyl, an optionally substituted heterocyclyl group or —N=CR$^{23}$R$^{24}$ where $R^{23}$ and $R^{24}$ are as defined for $R^1$; and $R^8$ to $R^{22}$ each independently represents an optionally substituted hydrocarbyl, a perhalogenated hydrocarbyl or an optionally substituted heterocyclyl group, one or more of $R^1$ & $R^6$, $R^2$ & $R^7$, $R^6$ & $R^7$, $R^6$ & $R^8$, $R^6$ & $R^{10}$, $R^6$ & $R^{12}$, $R^1$ & $R^8$, $R^2$ & $R^9$, $R^8$ & $R^9$, $R^8$ & $R^{10}$, $R^8$ & $R^{12}$, $R^1$ & $R^{10}$, $R^2$ & $R^{11}$, $R^{10}$ & $R^{11}$, $R^{10}$ & $R^{12}$, $R^1$ & $R^{12}$, $R^2$ & $R^{13}$, $R^{12}$ & $R^{13}$, $R^1$ & $R^{14}$ $R^2$ & $R^{15}$, $R^{14}$ & $R^{15}$, $R^{12}$ & $R^{14}$, $R^1$ & $R^{16}$, $R^1$ & $R^{16}$, $R^1$ & $R^{18}$, $R^1$ & $R^{19}$, $R^1$ & $R^{20}$, $R^2$ & $R^{21}$, $R^{20}$ & $R^{21}$ and $R^{21}$ & $R^{22}$ optionally being linked in such a way as to form an optionally substituted ring(s), and wherein the transfer hydrogenation catalyst is of general formula:

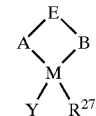

wherein:

$R^{27}$ represents a neutral optionally substituted hydrocarbyl, a neutral optionally substituted perhalogenated hydrocarbyl, or an optionally substituted cyclopentadienyl ligand;

A represents —NR$^{28}$—, —NR$^{29}$—, —NHR$^{28}$, —NR$^{28}$R$^{29}$ or —NR$^{29}$R$^{30}$ where $R^{28}$ is H, C(O)R$^{30}$, SO$_2$R$^{30}$, C(O)NR$^{30}$R$^{34}$, C(S)NR$^{30}$R$^{34}$, C(=NR$^{34}$) SR$^{35}$ or C(=NR$^{34}$)OR$^{35}$, $R^{29}$ and $R^{30}$ each independently represents an optionally. substituted hydrocarbyl, perhalogenated hydrocarbyl or an optionally substituted heterocyclyl group, and $R^{34}$ and $R^{35}$ are each independently hydrogen or a group as defined for $R^{30}$;

B represents —O—, —OH, OR$^{31}$, —S—, —SH, SR$^{31}$, —NR$^{31}$—, —NR$^{32}$—, —NHR$^{32}$, —NR$^{31}$R$^{32}$, —NR$^{31}$R$^{33}$, —PR$^{31}$— or —PR$^{31}$R$^{33}$ where $R^{32}$ is H, C(O)R$^{33}$, SO$_2$R$^{33}$, C(O)NR$^{33}$R$^{36}$, C(S)NR$^{33}$R$^{36}$, C(=NR$^{36}$)SR$^{37}$ or C(=NR$^{36}$)OR$^{37}$, $R^{31}$ and $R^{33}$ each independently represents an optionally substituted hydrocarbyl, perhalogenated hydrocarbyl or an optionally substituted heterocyclyl group, and $R^{36}$ and $R^{37}$ are each independently hydrogen or a group as defined for $R^{33}$;

E represents a linking group;

M represents a metal capable of catalysing transfer hydrogenation; and

Y represents an anionic group, a basic ligand or a vacant site;

2. A process for the production of primary or secondary amines of formula (3)

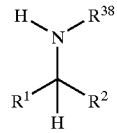
(3)

comprising the steps of
a) generating a substrate of general formula (1) from a carbonyl compound (2),

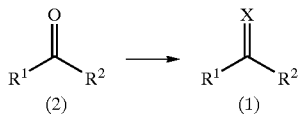

in which X represents $NR^3$ or $(NR^4R^5)^+Q^-$, and $Q^-$ represents a monovalent anion,
b) reacting the substrate of general formula (1) with a hydrogen donor in the presence of a transfer hydrogenation catalyst, and
c) removing $R^3$ or $R^4$ to give an amine of formula (3)

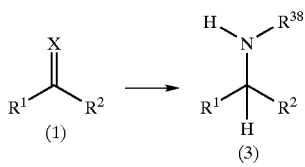

wherein:
$R^1$ and $R^2$ each independently represents a hydrogen atom, an optionally substituted hydrocarbyl, a perhalogenated hydrocarbyl, an optionally substituted heterocyclyl group, a substituted carbonyl functional group, a substituted thiocarbonyl functional group or substituted imino functional group, $R^1$ & $R^2$ optionally being linked in such a way as to form an optionally substituted ring;
$R^3$ and $R^4$ represents —P(O)$R^6R^7$, —P(O)$OR^8OR^9$, —P(O)$OR^8OH$, —P(O)(OH)$_2$, (OH)$_2$, —P(O)$SR^{10}SR^{11}$, —P(O)$SR^{10}SH$, —P(O)(SH)$_2$, —P(O)$NR^{12}R^{13}NR^{14}R^{15}$, —P(O)$NR^{12}R^{13}NHR^{14}$, —P(O)$NHR^{12}NHR^{14}$, —P(O)$NR^{12}R^{13}NH_2$, —P(O)$NHR^{12}NH_2$, —P(O)(NH$_2$)$_2$, —P(O)$R^6OR^8$, —P(O)$R^6OH$, —P(O)$R^6SR^{10}$, —P(O)$R^6SH$, —P(O)$R^6NR^{12}R^{13}$, —P(O)$R^6HR^{12}$, —P(O)$R^6NH_2$, —P(O)$OR^8SR^{10}$, —P(O)$OR^8SH$, —P(O)$OHSR^{10}$, —P(O)$OHSH$, —P(O)$OR^8NR^{12}R^{13}$, —P(O)$OR^8NHR^{12}$, —P(O)$OR^8NH_2$, —P(O)$OHNR^{12}R^{13}$, —P(O)$OHNHR^{12}$, —P(O)$OHNH_2$, —P(O)$SR^{10}NR^{12}R^{13}$, —P(O)$SR^{10}NHR^{12}$, —P(O)$SR^{10}NH_2$, —P(O)$SHNR^{12}R^{13}$, —P(O)$SHNHR^{12}$, —P(O)$SHNH_2$, —P(S)$R^6R^7$, —P(S)$OR^8OR^9$, —P(S)$OR^8OH$, —P(S)(OH)$_2$, —P(S)$SR^{10}SR^{11}$, —P(S)$SR^{10}SH$, —P(S)(SH)$_2$, —P(S)$NR^{12}R^{13}NR^{14}R^{15}$, —P(S)$NR^{12}R^{13}NHR^{14}$, —P(S)$NHR^{12}NHR^{14}$, —P(S)$NR^{12}R^{13}NH_2$, —P(S)$NHR^{12}NH_2$, —P(S)(NH$_2$)$_2$, —P(S)$R^6OR^8$, —P(S)$R^6OH$, —P(S)$R^6SR^{10}$, —P(S)$R^6SH$, —P(S)$R^6NR^{12}R^{13}$, —P(S)$R^6NHR^{12}$, —P(S)$R^6NH_2$, —P(S)$OR^8SR^{10}$, —P(S)$OHSR^{10}$, —P(S)$OR^8SH$, —P(S)$OHSH$, —P(S)$OR^8NR^{12}R^{13}$, —P(S)$OR^8NHR^{12}$, —P(S)$OR^8NH_2$, —P(S)$OHNR^{12}R^{13}$, —P(S)$OHNHR^{12}$, —P(S)$OHNH_2$, —P(S)$SR^{10}NR^{12}R^{13}$, —P(S)$SR^{10}NHR^{12}$, —P(S)$SR^{10}NH_2$, —P(S)$SHNR^{12}R^{13}$, —P(S)$SHNHR^{12}$, —P(S)$SHNH_2$, —P$R^6R^7$, —PO$R^8OR^9$, —PS$R^{10}SR^{11}$, —PN$R^{12}R^{13}NR^{14}R^{15}$, —P$R^6OR^8$, —P$R^6SR^{10}$, —P$R^6R^{12}R^{13}$, —PO$R^8SR^{10}$, —PO$R^8NR^{12}R^{13}$, —PS$R^{10}NR^{12}R^{13}$, —S(O)$R^{16}$, —S(O)$_2R^{17}$, —COR$^{18}$, —CO$_2R^{19}$, or SiR$^{20}R^{21}R^{22}$;

$R^5$ and $R^{38}$ represents a hydrogen atom, an optionally substituted hydrocarbyl, a perhalogenated hydrocarbyl, or an optionally substituted heterocyclyl group;

$R^6$ and $R^7$ independently represent an optionally substituted hydrocarbyl, a perhalogenated hydrocarbyl, an optionally substituted heterocyclyl group or —N=CR$^{23}R^{24}$ where $R^{23}$ and $R^{24}$ are as defined for $R^1$; and $R^8$ to $R^{22}$ each independently represents an optionally substituted hydrocarbyl, a perhalogenated hydrocarbyl or an optionally substituted heterocyclyl group, one or more of $R^1$ & $R^6$, $R^2$ & $R^7$, $R^6$ & $R^7$, $R^6$ & $R^8$, $R^6$ & $R^{10}$, $R^6$ & $R^{12}$, $R^1$ & $R^8$, $R^2$ & $R^9$, $R^8$ & $R^9$, $R^8$ & $R^{10}$, $R^8$ & $R^{12}$, $R^1$ & $R^{10}$, $R^2$ & $R^{11}$, $R^{10}$ & $R^{11}$, $R^{10}$ & $R^{12}$, $R^1$ & $R^{12}$, $R^2$ & $R^{13}$, $R^{12}$ & $R^{13}$, $R^1$ & $R^{14}$, $R^2$ & $R^{15}$, $R^{14}$ & $R^{15}$, $R^{12}$ & $R^{14}$, $R^1$ & $R^{16}$, $R^1$ & $R^{18}$, $R^1$ & $R^{19}$, $R^1$ & $R^{20}$, $R^2$ & $R^{21}$, $R^{20}$ & $R^{21}$ and $R^{21}$ & $R^{22}$ optionally being linked in such a way as to form an optionally substituted ring(s), and
the transfer hydrogenation catalyst is of general formula:

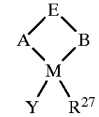

wherein:
$R^{27}$ represents a neutral optionally substituted hydrocarbyl, a neutral optionally substituted perhalogenated hydrocarbyl, or an optionally substituted cyclopentadienyl ligand;
A represents —NR$^{28}$—, —NR$^{29}$—, —NHR$^{28}$, —NR$^{28}R^{29}$ or —NR$^{29}R^{30}$ where $R^{28}$ is H, C(O)R$^{30}$, SO$_2R^{30}$, C(O)NR$^{30}R^{34}$, C(S)NR$^{30}R^{34}$, C(=NR$^{34}$)SR$^{35}$ or C(=NR$^{34}$)OR$^{35}$, $R^{29}$ and $R^{30}$ each independently represents an optionally substituted hydrocarbyl, perhalogenated hydrocarbyl or an optionally substituted heterocyclyl group, and $R^{34}$ and $R^{35}$ are each independently hydrogen or a group as defined for $R^{30}$;
B represents —O—, —OH, OR$^{31}$, —S—, —SH, SR$^{31}$, —NR$^{31}$—, —NR$^{32}$—, —NHR$^{32}$, —NR$^{31}R^{32}$, —NR$^{31}R^{33}$, —PR$^{31}$— or —PR$^{31}R^{33}$ where $R^{32}$ is H, C(O)R$^{33}$, SO$_2R^{33}$, C(O)NR$^{33}R^{36}$, C(S)NR$^{33}R^{36}$, C(=NR$^{36}$)SR$^{37}$ or C(=NR$^{36}$)OR$^{37}$, $R^{31}$ and $R^{33}$ each independently represents an optionally substituted hydrocarbyl, perhalogenated hydrocarbyl or an optionally substituted heterocyclyl group, and $R^{36}$ and $R^{37}$ are each independently hydrogen or a group as defined for $R^{33}$;
E represents a linking group;
M represents a metal capable of catalysing transfer hydrogenation; and
Y represents an anionic group, a basic ligand or a vacant site;

provided that when Y is not a vacant site that at least one of A or B carries a hydrogen atom.

provided that when Y is not a vacant site that at least one of A or B carries a hydrogen atom.

3. A process according to claim 1 or claim 2, wherein M is a group VIII transition metal.

4. A process according to claim 1 or claim 2, wherein $R^{27}$ is an optionally substituted aryl; an optionally substituted alkene; or a cyclopentadienyl group substituted with between 3 and 5 substituents.

5. A process according to claim 1 or claim 2, in which B represents —O—, —OH, —OR$^{31}$—, —NR$^{31}$, —NR$^{32}$—, —NHR$^{32}$, —NR$^{31}$R$^{32}$, or —NR$^{31}$R$^{33}$, where R$^{32}$ is H, C(O)R$^{33}$, SO$_2$R$^{33}$, C(O)NR$^{33}$R$^{36}$, C(S)NR$^{33}$R$^{36}$, C(=NR$^{38}$)SR$^{37}$, or C(=NR$^{38}$)OR$^{37}$, R$^{31}$ and R$^{33}$ each independently represents an optionally substituted hydrocarbyl, perhalogenated hydrocarbyl or an optionally substituted heterocyclic group, and R$^{36}$ and R$^{37}$ are each independently hydrogen or a group as defined for R$^{33}$.

6. A process according to claim 5, wherein either or both of A or B is substituted with an acyl or sulphonyl group.

7. A process according to claim 5 in which A-E-B is one of the following:

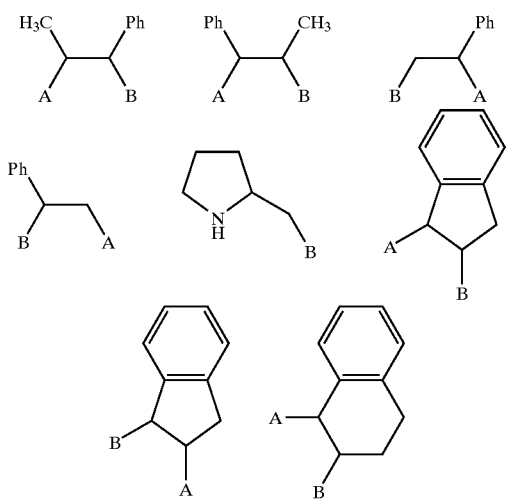

wherein A represents NR$^8$ or NHR$^8$, where R$^8$ is hydrogen, and B represents O or OH.

8. A process. according to claim 1 or claim 2, wherein $R^3$ or $R^4$ is a group selected from
—P(O)R$^6$R$^7$, —P(O)OR$^8$OR$^9$, —P(O)SR$^{10}$SR$^{11}$, —P(O)NR$^{12}$R$^{13}$NR$^{14}$R$^{15}$, —P(O)R$^6$OR$^8$, —P(O)R$^6$SR$^{10}$, —P(O)R$^6$NR$^{12}$R$^{13}$, —P(O)OR$^8$SR$^{10}$, —P(O)OR$^8$NR$^{12}$R$^{13}$, —P(O)SR$^{10}$NR$^{12}$R$^{13}$, —P(S)R$^6$R$^7$, —P(S)OR$^8$OR$^9$, —P(S)SR$^{10}$SR$^{11}$, —P(S)NR$^{12}$R$^{13}$NR$^{14}$R$^{15}$, —P(S)R$^6$OR$^8$, —P(S)R$^6$SR$^{10}$, —P(S)R$^6$NR$^{12}$R$^{13}$, —P(S)OR$^8$SR$^{10}$, —P(S)OR$^8$NR$^{12}$R$^{13}$, —P(S)SR$^{10}$NR$^{12}$R$^{13}$, —PR$^6$R$^7$, —POR$^8$OR$^9$, —PSR$^{10}$SR$^{11}$, —PNR$^{12}$R$^{13}$NR$^{14}$R$^{15}$, —PR$^6$OR$^8$, —PR$^6$SR$^{10}$, —PR$^6$NR$^{12}$R$^{13}$, —POR$^8$SR$^{10}$, —POR$^8$NR$^{12}$R$^{13}$, —PSR$^{10}$NR$^{12}$R$^{13}$, —S(O)R$^{16}$, —S(O)$_2$R$^{17}$, —COR$^{18}$, —CO$_2$R$^{19}$, and SiR$^{20}$R$^{21}$R$^{22}$.

9. A process according to claim 8 wherein $R^3$ or $R^4$ is —P(O)R$^6$R$^7$ or —P(O)OR$^8$OR$^9$.

10. A process according to claim 1 or claim 2, wherein the groups represented by $R^6$ to $R^{19}$ are independently selected from alkyl or aryl groups.

11. A process according to claim 1 or claim 2, wherein X is NR$^3$ where R$^3$ is either —P(O)R$^6$R$^7$ or —P(O)OR$^8$OR$^9$ and wherein R$^6$ to R$^9$ are independently selected from C$_{1-4}$alkyl groups, phenyl groups or phenyl groups substituted with one or more C$_{1-4}$alkyl groups.

12. A process according to claim 1 or claim 2, wherein the compound of formula (1) is prochiral, the transfer hydrogenation catalyst is chiral, an enantiomerically and/or diastereochemically purified form of catalyst being employed, whereby the compound of formula (1) is asymmetrically hydrogenated.

13. A process according to claim 1 or claim 2, wherein the hydrogen donor is selected from the group consisting of hydrogen, primary alcohols, secondary alcohols, primary amines, secondary amines, carboxylic acids, carboxylic acid esters, amine salts of carboxylic acids, readily dehydrogenatable hydrocarbons, clean reducing agents, and any combination thereof.

14. A process according to claim 13, in which the hydrogen donor is selected from the group consisting of propan-2-ol, butan-2-ol, triethylammonium formate and a mixture of triethylammonium formate and formic acid.

15. A process according to claim 3, wherein M is ruthenium, rhodium or iridium.

16. A process according to claim 4, wherein $R^{27}$ is a cyclopentadienyl group substituted with 5 substitutients.

17. A process according to claim 16, wherein $R^{27}$ is a pentamethylcyclo-pentadienyl group.

18. A process according to claim 5, in which A and B are linked through 2 optionally substituted carbon atoms and B represents —NR$^{31}$, —NR$^{32}$, —NHR$^{32}$, —NR$^{31}$R$^{32}$, or —NR$^{31}$R$^{33}$, where R$^{32}$ is H, C(O)R$^{33}$, SO$_2$R$^{33}$, C(O)NR$^{33}$R$^{36}$, C(S)NR$^{33}$R$^{36}$, C(=NR$^{38}$)SR$^{37}$, or C(=NR$^{38}$)OR$^{37}$, R$^{31}$ and R$^{33}$ each independently represent an optionally substituted hydrocarbyl, perhalogenated hydrocarbyl or an optionally substituted heterocyclic group, and R$^{36}$ and R$^{37}$ are each independently hydrogen or a group as defined for R$^{33}$.

19. A process according to claim 4, which A-E-B is one of the following:

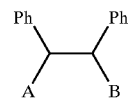

wherein:
A represents NR$^8$ or NHR$^8$, where R$^8$ is hydrogen, and
B represents NR$^{12}$ or NHR$^{12}$, R$^{12}$ is hydrogen, tosyl or —SO$_2$naphthyl;

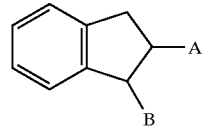

wherein:
A represents NR$^8$ or NHR$^8$, where R$^8$ is hydrogen, and
B represents NR$^{12}$ or NHR$^{12}$, R$^{12}$ is hydrogen or tosyl;

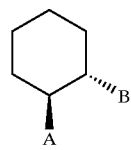

wherein:

A represents NR$^8$ or NHR$^8$, where R$^8$ is hydrogen, and
B represents NR$^{12}$ or NHR$^{12}$, R$^{12}$ is tosyl;
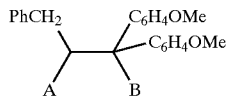
wherein:
A represents NR$^8$ or NHR$^8$, where R$^8$ is hydrogen, and
B represents NR$^{12}$ or NHR$^{12}$, R$^{12}$ is hydrogen.
20. A process according to claim 6, wherein the acyl or sulphonyl group is a toluenesulphonyl, methanesulphonyl, trifluoromethanesulphonyl or acetyl group.
* * * * *